(12) United States Patent
Shiuey et al.

(10) Patent No.: US 7,901,421 B2
(45) Date of Patent: Mar. 8, 2011

(54) SYSTEM FOR CUTTING THE CORNEA OF AN EYE

(75) Inventors: Yichieh Shiuey, San Jose, CA (US); Michael Rehal, Boulder Creek, CA (US)

(73) Assignee: Yichieh Shiuey, San Jose, CA (US)

( * ) Notice: Subject to any disclaimer, the term of this patent is extended or adjusted under 35 U.S.C. 154(b) by 1154 days.

(21) Appl. No.: 10/853,802

(22) Filed: May 24, 2004

(65) Prior Publication Data

US 2004/0243160 A1    Dec. 2, 2004

Related U.S. Application Data

(63) Continuation-in-part of application No. 10/445,065, filed on May 27, 2003, now Pat. No. 7,223,275.

(51) Int. Cl.
*A61F 9/007*      (2006.01)

(52) U.S. Cl. .................................................. 606/166

(58) Field of Classification Search ............ 606/166, 606/171, 177, 178, 107, 167, 130; 623/906, 623/5.11, 6.11, 6.12; 128/898; 600/424; 83/915.5

See application file for complete search history.

(56) References Cited

U.S. PATENT DOCUMENTS

| | | | | |
|---|---|---|---|---|
| 4,298,004 A | * | 11/1981 | Schachar et al. | 128/898 |
| 4,865,033 A | * | 9/1989 | Krumeich et al. | 606/166 |
| 5,135,530 A | * | 8/1992 | Lehmer | 606/107 |
| 5,215,104 A | * | 6/1993 | Steinert | 128/898 |
| 5,658,303 A | * | 8/1997 | Koepnick | 606/166 |
| 5,693,062 A | * | 12/1997 | Stegmann et al. | 606/166 |
| 5,779,723 A | | 7/1998 | Schwind | |
| 5,807,380 A | | 9/1998 | Dishler | |
| 5,944,731 A | | 8/1999 | Hanna | |
| 5,964,776 A | * | 10/1999 | Peyman | 606/166 |
| 6,022,365 A | | 2/2000 | Aufaure et al. | |
| 6,045,562 A | | 4/2000 | Amano et al. | |
| 6,045,563 A | | 4/2000 | Duprat | |
| 6,083,236 A | | 7/2000 | Feingold | |
| 6,126,668 A | | 10/2000 | Bair et al. | |
| 6,139,560 A | | 10/2000 | Kremer | |
| 6,228,099 B1 | | 5/2001 | Dybbs | |
| 6,277,134 B1 | * | 8/2001 | Amano et al. | 606/166 |
| 6,296,650 B1 | | 10/2001 | Carriazo | |
| 6,325,792 B1 | | 12/2001 | Swinger et al. | |

(Continued)

FOREIGN PATENT DOCUMENTS

EP      1620049 B1      2/2006

(Continued)

*Primary Examiner* — Anhtuan T Nguyen
*Assistant Examiner* — Kathleen Sonnett
(74) *Attorney, Agent, or Firm* — Kilpatrick Townsend & Stockton LLP

(57) ABSTRACT

A system for cutting the cornea of an eye, includes a moveable member with a cutting blade at one end, a pivot element and a cutting guide restraint. A mechanism for oscillating the moveable member around the pivot element and a cutting guide are configured to engage the cutting guide restraint on the moveable member and thereby limit the degree of angular movement of the cutting blade as the moveable member oscillates about the pivot element. A positioning system is configured to advance the moveable member with respect to the cutting guide such that the shape of the cutting guide determines the shape of a cut made by the cutting blade. A suction ring for stabilizing the cornea and an applanating plate for flattening the cornea usually complete the system.

9 Claims, 28 Drawing Sheets

U.S. PATENT DOCUMENTS

| | | |
|---|---|---|
| 6,332,890 B1 * | 12/2001 | Ortega et al. ............... 606/166 |
| 6,344,046 B2 | 2/2002 | Sugimura et al. |
| 6,358,260 B1 | 3/2002 | Ross et al. |
| 6,599,305 B1 | 7/2003 | Feingold |
| 6,723,106 B1 * | 4/2004 | Charles et al. ............... 606/130 |
| 2001/0004702 A1 * | 6/2001 | Peyman ....................... 606/166 |
| 2002/0045910 A1 | 4/2002 | Aufaure et al. |
| 2002/0091401 A1 | 7/2002 | Hellenkamp |
| 2007/0016234 A1 | 1/2007 | Daxer |

FOREIGN PATENT DOCUMENTS

| | | |
|---|---|---|
| WO | WO 2004/096106 A1 | 11/2004 |

* cited by examiner

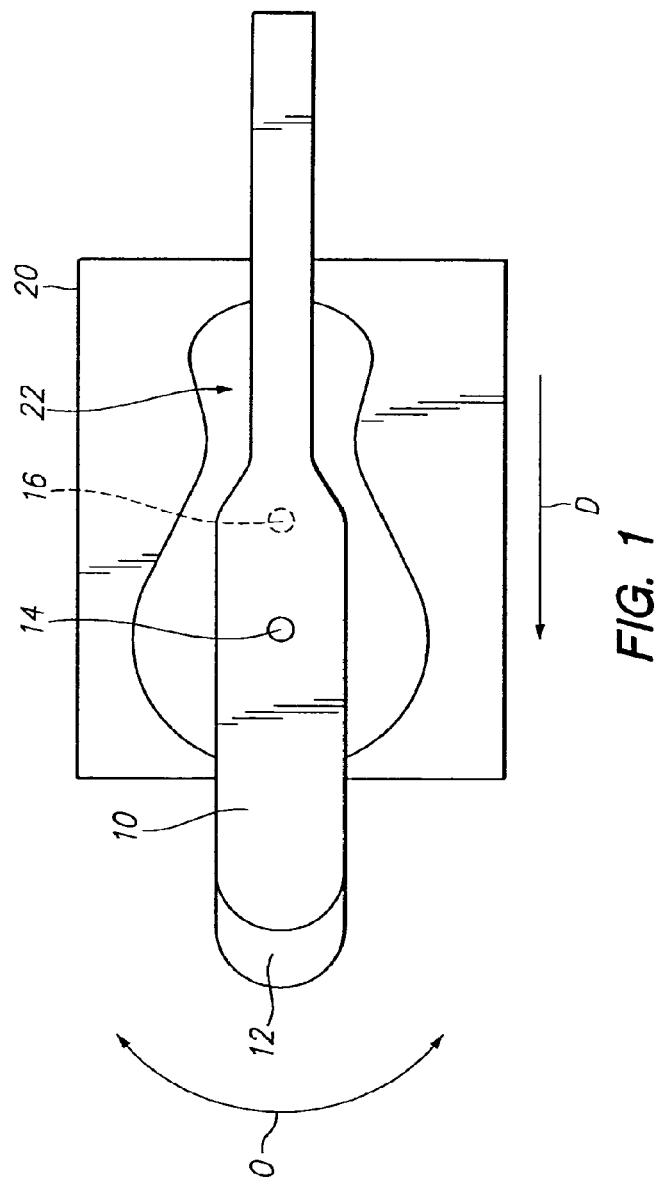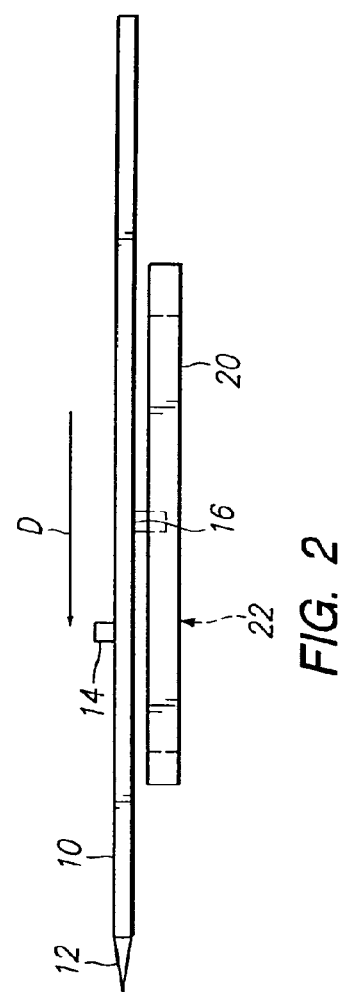

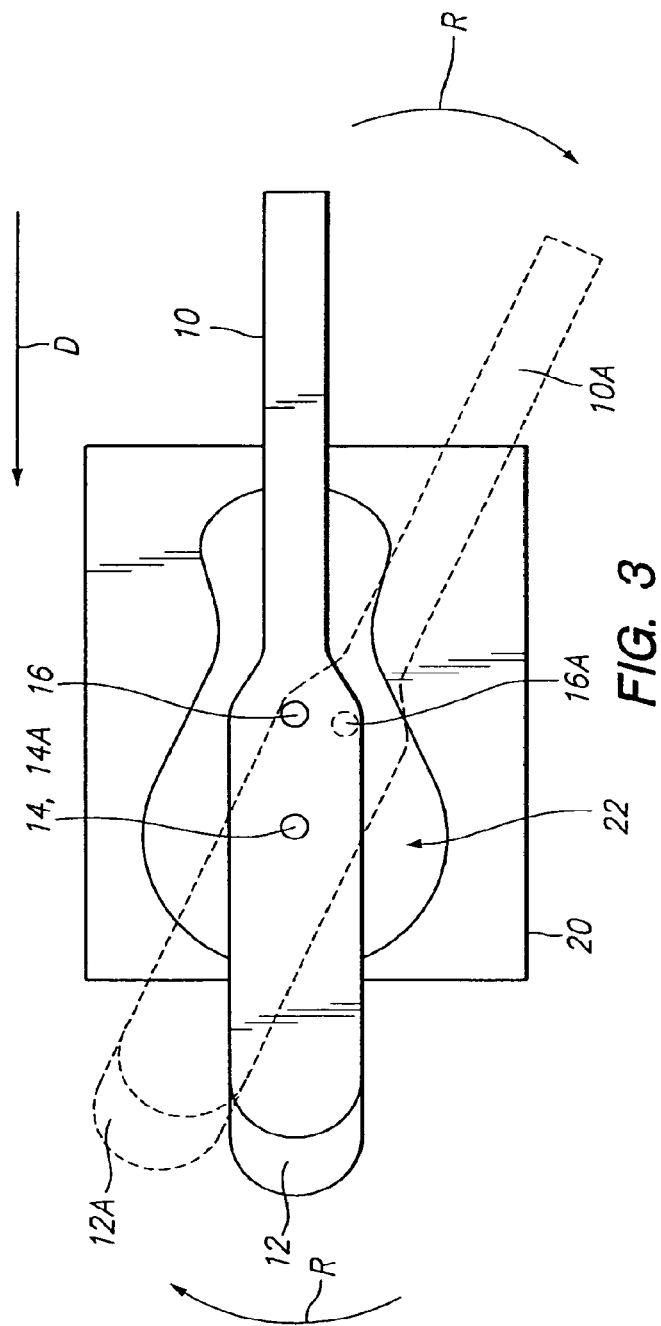
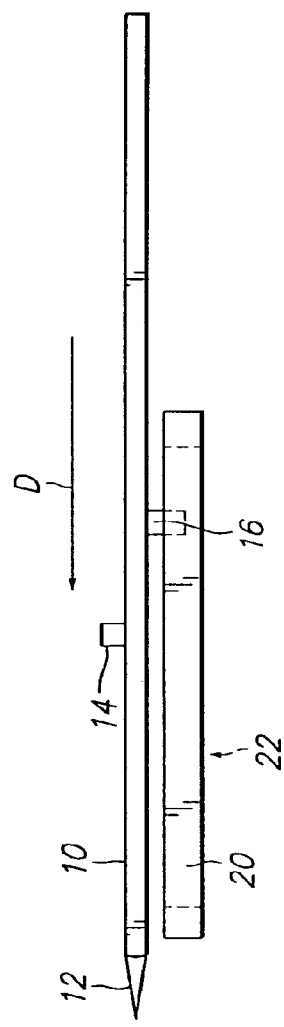
FIG. 3
FIG. 4

*(PRIOR ART COMPARISON)*

*(PRIOR ART COMPARISON)*

(PRIOR ART COMPARISON)

(PRIOR ART COMPARISON)

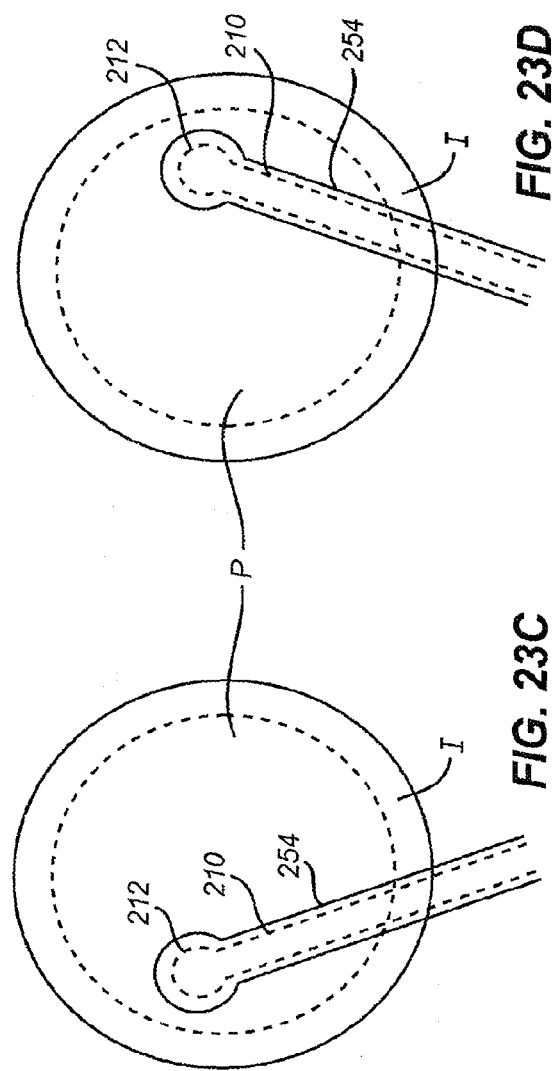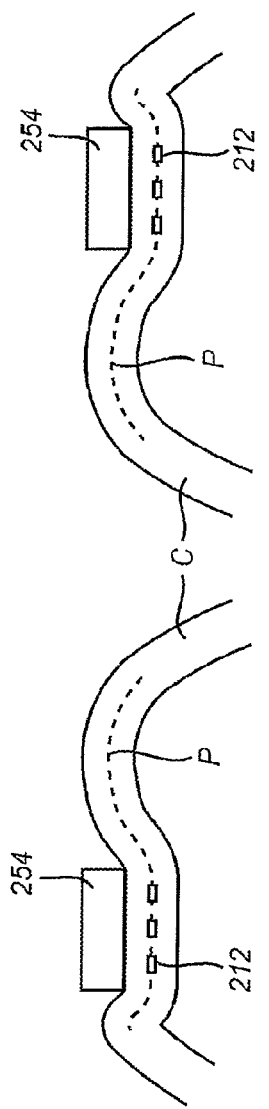

SYSTEM FOR CUTTING THE CORNEA OF AN EYE

CROSS-REFERENCES TO RELATED APPLICATIONS

This application is a continuation-in-part of U.S. patent application Ser. No. 10/445,065, filed May 27, 2003, now U.S. Pat. No. 7,223,275, the full disclosure of which is incorporated herein by reference.

BACKGROUND OF THE INVENTION

The present invention relates to surgical systems for cutting the cornea of a patient's eye.

The cornea is the clear cover of the eye and is also the main focusing lens in the eye. Disorders of the cornea, which adversely affect its shape or clarity, can cause loss of vision. Such disorders include Fuchs' endothelial dystrophy, pseudophakic bullous keratopathy, keratoconus, and herpes virus infection. When these conditions are severe the most common treatment is a full thickness corneal transplant which is also known as penetrating keratoplasty.

Penetrating keratoplasty is the removal of a full-thickness disk of diseased corneal tissue followed by the replacement of the diseased full-thickness disk of tissue by a full thickness disk of donated healthy corneal tissue. Currently, the diseased tissue is removed by the use of a non-automated or automated corneal trephine combined with manual excision using scalpels and or micro-surgical scissors. The disk of donated healthy corneal tissue is then secured to the recipient cornea by the means of sutures using micro-surgical techniques. Penetrating keratoplasty can provide dramatic improvements in vision in patients who have opacified or irregularly shaped corneas. Approximately, 40,000 corneal transplants are performed annually in the United States.

However, there are distinct disadvantages of penetrating keratoplasty. For example, penetrating keratoplasty has a long recovery time and typically takes between 6 to 12 months to achieve good vision. Moreover, because the donor corneal tissue is sutured manually, even in the hands of an experienced corneal surgeon, irregularities in the shape of the cornea frequently occur and can produce decreased vision because of induced astigmatism. The donated corneal tissue can also be rejected by the recipient's immune system with resulting loss of transparency of the donated cornea. Penetrating keratoplasty also has the potential for a devastating complication called expulsive suprachoroidal hemorrhage. In this complication, a spontaneous hemorrhage from the choroidal blood vessels behind the retina can occur during penetrating keratoplasty surgery after the diseased cornea has been removed and before the donor cornea has been sutured securely in place. Because the eye is open to atmospheric pressure in this situation, there is no normal intraocular pressure to stop the choroidal vessels from bleeding. The terrible result is that the retina, vitreous, and crystalline lens may be expulsed from the opening in the cornea resulting in blindness. This complication is estimated to occur approximately 1 in 500 cases with penetrating keratoplasty. Endophthalmitis (i.e. infection of the inside of the eye) is another serious complication that can occur and can also cause blindness if treatment is unsuccessful. Finally, after penetrating keratoplasty, the eye is very sensitive to injury, since the junction of the transplanted cornea and the recipient cornea can be easily disrupted with even mild trauma.

Because of the disadvantages of penetrating keratoplasty other methods of corneal surgery have recently been developed, as follows.

Lamellar keratoplasty is the general term for corneal surgeries that involve cutting within the layers (lamellae) of the cornea. Lamellar keratoplasty techniques allow removal and replacement of specific layers of the cornea. It is useful to be able to remove and transplant specific layers of the cornea because there are common corneal conditions that involve only certain layers of the cornea.

For example, a scar in the cornea from a herpes virus infection may affect only the superficial layers of the cornea. Removal and transplantation of the superficial layers of the cornea may be all that is necessary to restore sight to an eye that has a superficial scar and avoids many of the complications that can be associated with penetrating keratoplasty including endophthalmitis and expulsive suprachoroidal hemorrhage.

Another example would be Fuchs' endothelial dystrophy. The endothelium is the innermost layer of the cornea, which is responsible for pumping fluid out of the corneal tissues. This removal of fluid prevents the cornea from swelling and becoming opaque. In Fuchs' endothelial dystrophy, the endothelium is damaged and is unable to adequately pump fluid out of the cornea, which results in swelling and opacification of the cornea. Removal of the diseased inner layers of the cornea and transplantation with a layer of healthy tissue can restore clarity to the cornea and vision to the eye. By only exchanging the inner layers of tissue, the front surface of the cornea is essentially undisturbed. This decreases the likelihood of post-surgical astigmatism and may also result in less risk of rejection of the transplanted tissue.

A particular technique of lamellar keratoplasty is anterior lamellar keratoplasty. Anterior lamellar keratoplasty is a procedure where the superficial layers of the cornea are separated from the deeper layers with a hand held scalpel or an automated corneal surgical device called a microkeratome. Using this technique, a cap of the superficial layers of the cornea is removed and then replaced with a healthy cap from the superficial layers of the donor cornea.

Unfortunately, corneal tissue removal and replacement by the free hand method is extremely difficult to perform. Under the best of circumstances, it usually results in irregular astigmatism that is caused by irregularities in the thickness of the corneal tissue removed as well as in the thickness of the transplanted tissue. The irregular astigmatism typically limits the best spectacle corrected vision to no better than 20/40.

As stated above, automated anterior lamellar keratoplasty involves the excision of a cap of superficial corneal tissue by the use of a microkeratome. Similarly, the same apparatus can be used to prepare a cap of superficial donor corneal tissue for transplantation. The donor tissue is then sutured to the recipient cornea. The sutures are typically removed within the first few months to minimize astigmatism. Unfortunately, a problem that can occur with this technique is that the transplanted donor disk may be dislodged with relatively minor trauma, even after prolonged periods of time. This can occur because the cap of corneal tissue is only held in place by the relatively weak healing between the layers of donor and recipient tissue and there is no support against lateral or vertical pressure.

Another particular technique of lamellar keratoplasty is posterior lamellar keratoplasty. Posterior lamellar keratoplasty is a procedure where the deeper (i.e. rear) layers of the cornea are separated from the superficial layers with a hand held scalpel or an automated microkeratome. A disk of the deeper layers of the cornea is removed and then replaced with a healthy disk from the deeper layers of the donor cornea.

In the free hand posterior lamellar keratoplasty technique, a blade is manually used to create a pocket in the deep layers of the cornea. An internal manual trephine is then used to cut a disk of the deepest corneal layers. The disk of the deepest corneal layers is then excised with microsurgical scissors and or scalpels.

The donor corneal disk of the deepest corneal layers is then harvested by one of three methods.

In a first method a fresh whole donor eye is pressurized with balanced salt solution and a free hand dissection is used to create a pocket within the deep layers of the cornea. The donor disk of the deepest corneal layers is then excised with a trephine, microsurgical scissors, or scalpels. Difficulties with this method include the extremely tedious and difficult nature of the surgical dissection, the potential for inadvertently destroying the donor disk as part of the dissection, and the difficulty with finding a fresh human cadaveric donor eye that is available for surgery within 48 hours of the donor's time of death. Unlike excised donor corneas, whole donor eyes lose their viability to be used as donor tissue within 48 hours.

In a second method, a donor cornea and attached scleral rim is placed within a free standing anterior chamber maintainer. The donor cornea is then pressurized to maintain rigidity of the corneal tissue. A free hand dissection then ensues to create a partial thickness cornea of the deepest layers only. The disk of tissue is then excised using a trephine. Again, a significant problem with this method of harvesting donor tissue is that the free hand dissection is difficult and time consuming. There is also the risk of damaging the donor tissue through the dissection that renders it useless for transplantation.

In a third method, the donor cornea and attached scleral rim are placed within a free standing anterior chamber maintainer. The donor cornea is then pressurized to maintain rigidity of the corneal tissue. A separate prior art flap or cap making microkeratome that is adapted for use with the anterior chamber maintainer is used to create a flap or cap in the donor tissue. A disk of tissue is then excised from the partial thickness layers of the cornea that were created by the microkeratome. The primary problem with this method is that a separate prior art expensive flap or cap making microkeratome device is required to harvest the corneal tissue. Moreover, the flap or cap making microkeratome cannot be used to create the corneal pocket.

Once the disk of the deepest corneal layers is harvested, it is then placed inside the manually created pocket to fill the space of the excised corneal tissue. The transplanted disk of tissue initially stays in place by the pumping mechanism of the corneal endothelial cells and then gradually heals into place permanently. One significant advantage of this technique is that post-operatively, the eye is much less susceptible to injury than in other methods of corneal transplantation. Moreover, because the transplantation occurs within a pocket of the corneal tissues, the transplant is well protected by the intact boundaries of the corneal pocket. Unfortunately, a disadvantage of such free hand technique is that it is very difficult to manually create a pocket in the corneal tissues, wherein the pocket is of uniform depth. Rather, it is quite possible to either prematurely cut through the deepest layers of the cornea and thus enter the anterior chamber, or to accidentally cut too superficially and thus exit from the superficial cornea. The inability to create a uniform pocket will necessitate the abandonment of posterior lamellar keratoplasty and may require conversion to traditional penetrating keratoplasty.

Using a motorized microkeratome for posterior lamellar keratoplasty involves the creation of a flap of corneal tissue with a motorized blade. This is followed by excision of a disk of the deepest layers of the cornea including the endothelium. The excised disk of corneal tissue (including the endothelium) is replaced by the same layers from a donor cornea. The donated corneal disk is then secured in place with sutures. The corneal flap of the recipient cornea is also secured with sutures for up to several months. A disadvantage of this technique is that, like penetrating keratoplasty, the inside of the eye is exposed to atmospheric pressure and therefore there is also a risk of suprachoroidal hemorrhage with this technique. Another disadvantage is that post-operatively the eye is still fairly vulnerable to injury. For example, even minor trauma could result in flap dislocation or rupture of the transplant-recipient junction.

Recently anterior lamellar keratoplasty and posterior lamellar keratoplasty have also been performed on an experimental basis where the incisions have been created with a laser. Two disadvantages of this technique are the high cost of lasers and potential difficulty for the laser to create incisions in corneas that are scarred or opacified. See U.S. Pat. No. 6,325,792 to Swinger et al.

Ametropia, the incorrect focusing of light rays onto the retina, is the most common cause of decreased vision in humans. Common examples of ametropia include myopia, hyperopia or hypermetropia, and astigmatism. Because the cornea is the primary focusing lens in the eye, modification of the shape of the cornea by surgery has the ability to cause dramatic improvements in vision in patients that have ametropia.

LASIK (laser assisted in situ keratomileusis) is a method of laser vision correction that can dramatically improve vision by changing the shape of the cornea to allow the proper focus of light rays onto the retina. In the LASIK technique, a motorized blade is used to cut away a thin flap of tissue from the front of the cornea. The flap of corneal tissue is then lifted to expose the interior surface of the cornea. This exposed interior surface is then reshaped by the application of laser light. The flap of corneal tissue is then repositioned over the reshaped interior portion of the cornea. The flap initially stays in position through the natural pumping mechanism of the corneal endothelial cells and then gradually heals into place permanently. In this procedure, there is considerable variability in the size and shape of the laser treatment. However, with current corneal surgical devices the size and shape of the flap that covers the laser treatment is unfortunately rather limited. Another disadvantage of this procedure is that some corneal tissue is destroyed permanently as part of the vision correction process, due to the vaporization of corneal tissue by the laser.

Another vision improvement technique is keratophakia. Keratophakia is the insertion of a lens within the cornea. Keratophakia can also modify the curvature of the cornea for the purpose of improving a patient's vision. In Keratophakia, a pocket is made within the corneal tissues usually by means of a hand held blade. U.S. patent application Ser. No. 2001/0004702 to Peyman describes a non-motorized apparatus for creating such a pocket within the cornea. In the Peyman device, movement of the blade is created by manually twisting the blade. After the pocket is made within the corneal tissue, an organic or synthetic lens is implanted within the pocket to reshape the cornea in order to change the focus of light rays. The disadvantage of either a manual technique or a non-motorized technique is that the uniformity of the pocket is largely dependent on the surgeon's skill and experience and therefore there can be a high degree of variability. The Peyman device is designed only for the purpose of creating a pocket within the cornea of a living patient and cannot be used for the purpose of creating a pocket within a donor cornea.

U.S. Pat. No. 6,599,305 to Feingold describes a motorized apparatus for creating a pocket within the cornea for the purpose of lens implantation. In this invention, the blade assembly oscillates laterally while extending forward into the cornea to form the pocket, and the amplitude of the lateral oscillation increases as the blade goes beyond an entry incision into the cornea. A disadvantage of this method of automatically creating a pocket within the cornea is that the width of the entry incision will necessarily be relatively large compared to the width of the pocket. The Feingold device cannot create a pocket with an entry incision width that is less than half of the maximum width of the pocket. The Feingold device also cannot create a pocket that is more than twice the width of the cutting blade. Having a larger entry incision will cause slower healing, increase the risk of induced corneal astigmatism, and usually necessitate the need for suture closure. The Feingold device is designed exclusively for the purpose of creating a pocket within the cornea of a living patient and cannot be used for the purpose of creating a pocket within a donor cornea.

Because of the apparent difficulties with the current corneal surgical devices there is still a continuing need for an improved apparatus and method to create a pocket, flap, or a cap of corneal tissue in a live or donor cornea, wherein the pocket, flap, or cap is of uniform depth and thickness. In particular, it would be desirable to provide methods and systems for cutting cornea pockets where the ratio of pocket width to width of the entrance channel is maximized.

DESCRIPTION OF THE BACKGROUND ART

U.S. Pat. Nos. 6,599,305 B1 and 5,964,776, describe methods and apparatus for creating corneal pockets for implanting lenses. Other pertinent patents and published applications include U.S. Pat. Nos. 6,385,260; 6,344,046; 6,332,890; 6,325,792; 6,296,650; 6,277,134; 6,228,099; 6,139,560; 6,045,563; 6,045,562; 6,022,365; 5,944,731; 5,807,380; 5,779,723; and US2002/0,091,401; US2002/0045910; and US2001/0004702.

BRIEF SUMMARY OF THE INVENTION

Improved systems and methods for cutting the cornea of an eye, particularly for forming internal pockets in the eye, are provided. The systems and methods allow for corneal pocket formation using a relatively small initial incision while providing a pocket having a relatively large width or diameter.

Systems for cutting the cornea of an eye in accordance with the present invention comprise a frame, a moveable member having a cutting blade at a distal end thereof, and a driver coupled to the moveable member. The frame can be immobilized relative to the eye and will usually comprise a suction ring and an applanating plate. The driver is adapted to both translate and rotate the moveable member relative to the frame. By having such freedom of movement, motion of the moveable member can be limited within a relatively small entrance incision while motion of the cutting blade is relatively unrestricted.

In the exemplary embodiments, the moveable member is linear, but the moveable member could also be non-linear, for example being curved, curved-in-part, angulated, or having other non-linear configurations.

The moveable member may be suspended relative to the frame in a variety of ways. Most commonly, the moveable member will be positioned to rotate on a pivot, where the pivot can be translated and/or moved over a two-dimensional plane. Alternatively, the moveable member may be mounted a fixed pivot, where the moveable member can translate and/or rotate over the pivot. When the pivot translates, the path of translation may be linear or non-linear, typically being linear and aligned with a centerline through the frame. The pivot itself may comprise a pin or other protrusion to support the moveable member. In other embodiments, however, the "pivot" may comprise lateral restraints which allow the moveable member to translate while limiting lateral movement of the moveable arm at the point of the restraints, i.e., mimicking a pivotal support where the arm translates and rotates over the pivot.

In other embodiments, the moveable member will be manipulated on a "pivotless" system. Such pivotless systems may provide for essentially unlimited freedom of motion in a two-dimensional plane. Such drivers may comprise parallelogram linkages, cable supports, and other known mechanical drive systems.

In all cases, the moveable arm may be manually positioned, often using a template or other motion guide. In the presently preferred embodiments, however, the moveable arm will be driven by a powered system, typically a motor, which is automatically controlled using a computer, programmable controller, or other control system which can be programmed to achieve a precise and selectable pocket size.

The systems of the present invention will be particularly useful for performing corneal transplants. In such cases, the systems will frequently further comprise an anterior chamber maintainer which can be used to hold a donor cornea prior to harvesting the corneal implant. In particular, the anterior chamber maintainer will be adapted for use together with the moveable member, cutting blade, and driver in place of the corneal frame. In that way, the implant which is cut from the donor cornea will precisely match the thickness of the hole which is cut by the same system when used on the cornea with the frame. The peripheral dimensions of the implant will, of course, be determined by the separate cutting blade which is used for both the donor cornea and the recipient cornea.

The present invention further provides methods for forming a pocket in a cornea. The methods comprise advancing a cutting element at a distal end of a moveable member through an entry incision in the cornea. Movement of the movable member is controlled to cause the cutting element to create a pocket having a width in at least one direction through a center of the cornea which is greater than twice a width of the entry incision. Usually, the entry incision has a width which is no greater than 4 mm and the pocket has a width which is greater than 8 mm. Preferably, the pocket will have a width of at least 8 mm, and in some cases the width will be at least 10 mm.

The ratio of the pocket width or diameter relative to the entry incision width can be maximized by using a moveable member having a relatively narrow width, at least at a region through which the member passes through the entry incision. Usually, the width will be no greater than 1 mm over this region.

Controlling the moveable member typically comprises both translating and rotating the moveable member relative to the cornea. Such translating and rotating can be achieved in a number of ways, generally as described above in connection with the systems of the present invention. Briefly, the moveable member may be rotated on a pivot point, where the pivot point is capable of being translated and/or the moveable member may translate over the pivot point. In other embodiments, the pivot point may be fixed relative to the cornea and the moveable member translated over or under the pivot point. In addition to being useful for performing corneal transplantation, the methods of the present invention can be used for implanting a lens in the pocket which is formed. Frequently, the lens will restrained to pass through the narrow width entry incision and released to its expanded configuration within the pocket. The methods, of course, are also useful for implanting a corneal graft in the pocket as generally described above.

In yet another aspect of the present invention, a method for cutting a pocket in a cornea comprises advancing a cutting element at the distal end of a moveable member through an entry incision into the cornea. Movement of the moveable member is controlled to cause the cutting element to create a pocket, where the moveable member is both rotated and translated relative to the cornea. The rotation and translation of the moveable member may be achieved by any of the techniques described above using a pivot point or using a pivotless driver. Preferred dimensions of the entry incision and ratios between the width of the entry incision and dimensions of the corneal pocket have also been described previously.

In a still further aspect of the present invention, methods for transplanting a cornea comprise creating a pocket in the cornea of the patient, where the pocket has an entry incision with a width less than that of the pocket. A cylinder of tissue is removed from over or under the pocket while the remaining portions of the corneal tissue remain intact to limit exposure of the interior of the eye to atmospheric pressure. The removed cylinder of tissue may then be replaced with donor tissue, where the interior of the cornea remains protected from exposure to the atmospheric pressure. The procedure is useful for both anterior lamellar keratoplasty and posterior lamellar keratoplasty. The pocket is typically created by advancing a blade into the cornea while flattening the cornea with an applanator. Optionally, the donor tissue may be harvested with the same pocket making device that was used to create the pocket in the recipient cornea. In such instances, the donor cornea may be supported on an anterior chamber maintainer which the cornea is cut with the cutting element.

In an additional aspect of the system of the present invention, an anterior chamber maintainer for harvesting a donor cornea comprises a support for the donor cornea useful while a pocket forming device creates a pocket within the donor cornea.

The inventions described above provide a number of advantages and benefits. In preferred aspects, the present invention provides a system for cutting the cornea of an eye, comprising a moveable member that may be translated or rotated within a plane in a non-manual or manual fashion, a cutting element at one end of the moveable member, a suction ring for stabilizing the cornea, and an applanator for flattening the cornea.

In preferred aspects, the moveable member has a cutting blade at one end, a pivot element disposed thereon, a cutting guide restraint disposed thereon, a mechanism for oscillating the moveable member around the pivot element, a cutting guide software program which controls a programmable motor that engages the cutting guide restraint on the moveable member and thereby limits the degree of angular movement of the cutting blade as the moveable member rotates about the pivot element, and a cutting guide software controlled positioning system configured to advance the moveable member with respect to the cornea In further preferred aspects of the invention, the moveable member, cutting element, suction ring, and applanator are all disposable.

In still further preferred aspects, the cutting element may be a solid blade or any other cutting mechanism appropriate to cut the cornea e.g. electromagnetic energy such as a laser or plasma field.

In alternate preferred aspects of the invention, the pivot element of the moveable member may be adjustably or selectively positioned relative to the cutting path. Adjusting the position of the pivot element allows the cutting blade to move within a pocket that has a small opening.

In one embodiment, the position of the pivot element is determined by a cutting guide software program that commands a programmable motor to move the pivot element along a specified path. The path of the pivot element of the moveable member may be either linear or non-linear.

Other embodiments can be envisioned where the movement of the pivot element is controlled by wires, pistons, pneumatics, or magnetism, these are all within the scope of the present invention. In additional preferred aspects, the angles of the cutting guide restraint and the cutting blade are determined by the relative position of the pivot element of the moveable member and a restraining element engaged to the cutting restraint.

In preferred aspects the cutting blade is able to create a pocket with an internal maximum width that is larger than twice the entry incision width.

In further preferred aspects of the invention, the moveable member may have a fixed pivot point relative to the cornea. The moveable member may translate over or under the pivot point as well as rotate around the pivot point while a cutting element attached to one end of the moveable member creates a cut in the cornea.

In alternative preferred aspects, the moveable member may have a fixed pivot point relative to the cornea and the moveable member is able to shorten and lengthen its portion that is proximal to the cornea while a cutting element attached to one end of the moveable member creates a cut in the cornea.

In other alternate preferred aspects of the invention, the moveable member may have no pivot element. The angular position of the moveable may be determined by applying a pushing or pulling force to at least one point on each side of the moveable member. Angular and translational positioning of the moveable member may be achieved by any form of a mechanical, electrical, magnetic or pneumatic system, but the present invention is not so limited.

In yet other preferred aspects, the cutting element may be deformable in shape and size. This advantageously allows a larger pocket to be created through a relatively small opening.

In still more preferred aspects of the invention, one or all of the following components are disposable: the cutting guide, the mechanism for oscillating the moveable member, the applantor, and the suction ring.

In yet more preferred aspects, the cutting guide software determines the shape of a cut made by the cutting blade by simultaneously controlling the angle of the cutting blade and the relative position of the cutting blade to the cornea. The cutting guide software program controls the angle and position of the blade by giving commands to one or more programmable motors such as a stepper or servo motor to change the angle of the blade as the blade is advanced into the cornea by a programmable drive motor.

In additional alternate preferred aspects, the mechanism for oscillating the moveable member around the pivot element may comprise any form of a mechanical, electrical, magnetic or pneumatic system, but the present invention is not so limited.

In yet additional alternate preferred aspects, the positioning system that moves the moveable member relative to the cutting guide may comprise any form of a mechanical, electrical, magnetic or pneumatic system, but the present invention is not so limited.

In specific aspects of the invention, the present invention also provides a method of cutting a cornea, including: penetrating a cornea with a cutting element at one end of a moveable member; non-manually moving or rotating a moveable within a plane; and advancing the moveable member with respect to the cornea, thereby cutting the cornea with the cutting blade.

In preferred aspects, a pivot point of the moveable member is advanced with respect to the cornea in order to advance the blade into the cornea. In one embodiment, the position of the pivot point may be adjusted in a controlled fashion by a linkage to a programmable motor. In another embodiment, no pivot element is used and the angle and position of the moveable member is not limited by a pivot point. In further preferred aspects, the cornea is stabilized with a suction ring; and the front surface of the cornea is flattened with an applanator prior to penetrating the cornea with the cutting blade. In alternate preferred aspects, a donor cornea is stabilized prior to cutting by an optional anterior chamber maintainer that attaches to the present invention.

In preferred aspects, the path of the moveable member may either be linear or non-linear as it cuts the cornea. An example of a non-linear path would be an arcuate path. In one embodiment of the device, the moveable member is rotated into the cornea as it oscillates to create the pocket.

In different embodiments, the applanator may be held at a fixed position as the cutting blade cuts through the cornea, or the applanator may be advanced across the cornea as the cutting blade cuts through the cornea. The applanator may be in the form of a plate that can flatten the majority of the cornea or it may be an applanator that is only sufficiently large to flatten the portion of the cornea that is being cut. The applanator may also move in conjunction with the cutting blade, so that the portion of the cornea that is to be cut will be flattened in advance of the cutting blade.

Accordingly, the present invention provides a system and method of creating a pocket of uniform depth in the cornea. The pocket can be made of various shapes and sizes, between various layers of a live or donor cornea.

One advantage of the present system is that it is able to create a pocket of uniform depth within the cornea. Another advantage of the present system is that it is able to create a cut into the cornea wherein the cut has an external opening that is smaller than the internal dimensions of the pocket. In particular, the present system is able to automatically or manually create a pocket with an external incision width that is smaller than half of the maximum pocket width, e.g., larger than twice the width of the cutting blade.

Accordingly, the present invention may be used to transplant a portion of the inner layer of the cornea with a number of advantages. A significant safety advantage is that the transplantation may occur in a relatively closed system protected from atmospheric pressure. This reduces the risk of expulsive suprachoroidal hemorrhage. Being able to create a relatively large pocket also has the advantage of being able to transplant a larger section of the donor cornea with a corresponding larger number of healthy corneal endothelial cells. Additionally, having the external opening smaller than the internal dimensions of the pocket will also make the eye much more resistant to trauma than would be the case in penetrating keratoplasty. Moreover, the ability to make a small external opening will increase the speed of healing, decrease surgically induced astigmatism, and allows sealing of the wound without the use of sutures.

The present invention also allows the convenient harvesting of a donor graft for both anterior and posterior lamellar keratoplasty. The optional anterior chamber maintainer device allows the creation of a pocket within a donor cornea. A disk of donor tissue from above or below the pocket can then be excised with scissors or a trephine for the purpose of anterior or posterior lamellar keratoplasty. Advantageously, the same pocket making device that is used to create a pocket within the layers of the recipient cornea may be used to harvest the donor corneal tissue, thus increasing the ease of the procedure and eliminating the expense of purchasing a separate device to harvest the donor corneal tissue.

The present invention also describes an anterior chamber maintainer that may be adapted to function with any pocket forming device such as those described by Peyman in U.S. Pat. Application 20010004702 and Feingold in U.S. Pat. No. 6,599,305 to allow harvesting of donor corneal tissue.

The present invention may also be used to insert a reversibly deformable lens into the cornea. Having an external opening that is smaller than the internal dimensions of the pocket will help protect against extrusion of the lens. Having a larger pocket area also has the advantage of being able to insert a larger lens, which can result in improved vision especially for patients that have large pupils. Specifically, a pocket which has a width that is larger than at least 5 mm will be able to contain a lens that is at least 5 mm in diameter. A lens inserted within the cornea with a diameter of at least 5 mm is more likely to be compatible with acceptable vision than a lens smaller than 5 mm. Moreover, the ability to make a small external opening will increase the speed of healing, decrease surgically induced astigmatism, and allows sealing of the wound without the use of sutures.

The reversibly deformable lens may be folded or squeezed by forceps to allow entry through the small external opening. The deformable lens may also be composed of a thermally reactive polymer that allows the implant to be in a shape that easily fits through the small external opening at room temperature (e.g. a rod) and then allows the implant to change into a final shape (e.g. a disk) that is well retained within the pocket. In preferred aspects the deformable intracorneal lens should be bio-compatible with the cornea and will allow diffusion of oxygen, carbon dioxide, other gases, glucose and other nutrients through the implanted lens and cornea.

BRIEF DESCRIPTION OF THE DRAWINGS

FIG. 1 is a top plan view of the moveable member and associated cutting guide.

FIG. 2 is a side elevation view corresponding to FIG. 1.

FIG. 3 is a view similar to FIG. 1, but additionally showing (in dotted lines) the moveable member moved to a second position at which a cutting guide restraint on the moveable member contacts a side of the cutting guide.

FIG. 4 is a side elevation view corresponding to FIG. 3.

FIGS. 23C-23F illustrate movement of the cutting blade in the systems of FIGS. 23A and 23B as illustrated.

DETAILED DESCRIPTION OF THE INVENTION

In preferred aspects, the present invention provides a corneal surgery system that can be used to cut a live or donor cornea to form a pocket, flap or cap by separating the layers of the cornea. Specifically, the present invention provides a system for automatically creating a pocket of uniform depth, which can be of various shapes and sizes, between the layers of a live or donor cornea. The present invention may also be used to create a flap or cap of corneal tissue in a live or donor cornea.

In accordance with the present invention, a system for cutting a cornea is provided. The system comprises a cutting blade that is moved back and forth in an arcuate path while simultaneously being advanced to cut through a cornea. As will be explained, the degree of angular movement of the cutting blade is limited by contacts between a moveable member (to which the cutting blade is attached) and a cutting guide.

Operation of the present invention can be understood by reference to FIGS. 1 to 5 which illustrate the movement of the moveable member with respect to the cutting guide.

FIGS. 6A to 7C and 9 and 10 show further details of various embodiments of the present invention.

Figure 8A:
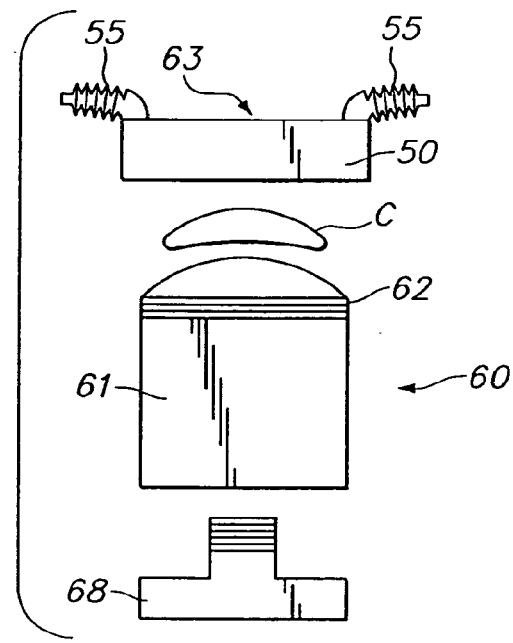
FIG. 8A is a side elevation view of an optional anterior chamber maintainer that may be affixed to the suction ring of the present invention.
Figure 8B:
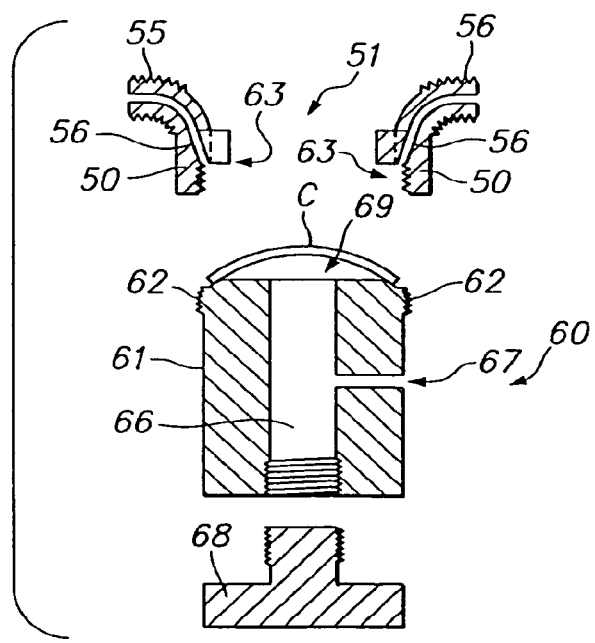
FIG. 8B is a sectional side elevation view corresponding to FIG. 8A, showing inner workings of the anterior chamber maintainer.

FIGS. 8A and 8B show an optional attachment device that can be used with various embodiments of the present invention.

Figure 11:
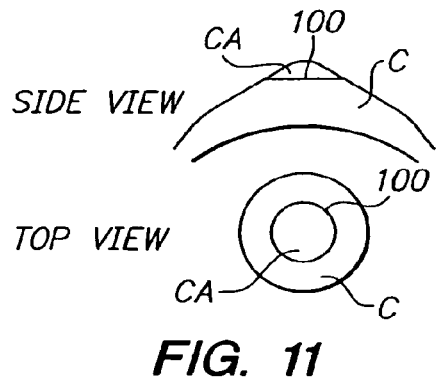
FIG. 11 is corresponding side and top views of anterior lamellar keratoplasty procedure performed with prior art techniques.
Figure 12:
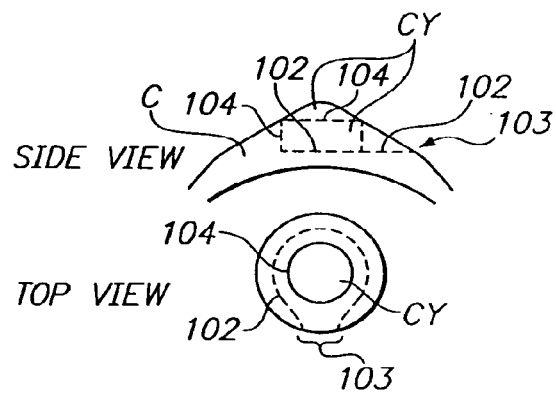
FIG. 12 is corresponding side and top views of anterior lamellar keratoplasty procedure performed with a technique in accordance with the present invention.
Figure 13:
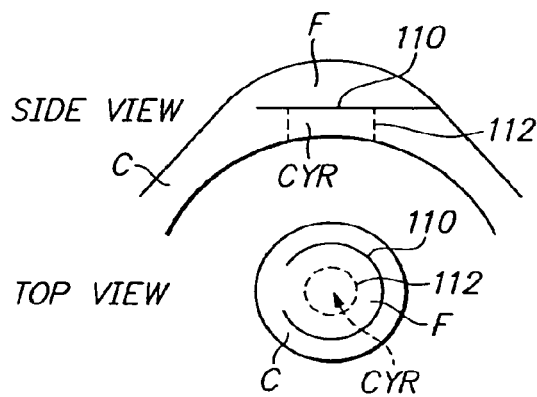
FIG. 13 is corresponding side and top views of a posterior keratoplasty procedure performed with prior art techniques.
Figure 14:
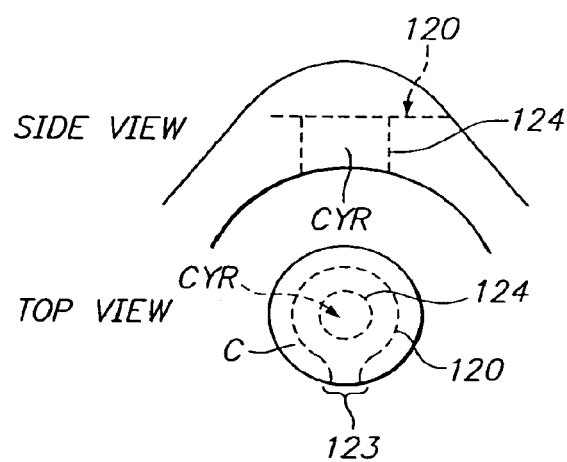
FIG. 14 is corresponding side and top views of a posterior keratoplasty procedure performed with a technique in accordance with the present invention.

Lastly, FIGS. 11 and 13 show surgical cutting procedures performed by pre-existing techniques. FIGS. 12 and 14 show comparable surgical cutting procedures performed with the system of the present invention.

Referring first to FIGS. 1 and 2, a moveable member 10 is provided. Moveable member 10 has a cutting blade 12 at one end. In optional aspects, cutting blade 12 may be made of steel, stainless steel, sapphire, diamond, plastic or ceramic, but is not so limited. Rather, any material suitable for cutting the cornea may be used. Moveable member 10 has a pivot 14 thereon. As will be shown, moveable member 10 is oscillated such that it sweeps back and forth in an angular path of direction O about its pivot 14. Moveable member 10 further includes a cutting guide restraint 16 projecting therefrom. Cutting guide restraint 16 is received with a hole 22 of a cutting guide 20.

As shown in FIGS. 2 and 4, cutting guide restraint 16 projects from the bottom of moveable member 10 and cutting guide 20 is positioned below moveable member 10. The present invention is not so limited. Alternate embodiments are possible, all keeping within the scope of the present invention. For example, cutting guide restraint 16 may instead project from the top of the moveable member with cutting guide 20 being placed above moveable member 10. Other designs are also possible.

In accordance with the present invention, corneal cutting is performed by angular back and forth movement (i.e.: oscillation in direction O) of moveable member 10 about pivot 14 at the same time that pivot 14 is advanced in direction D with respect to cutting guide 20. As moveable member 10 is advanced in direction D, cutting guide restraint 16 will contact successive locations around the sides of hole 22 in cutting guide 20. The novel shape of hole 22 in cutting guide 20 will have the effect of limiting the degree of angular (i.e., side to side) motion of cutting blade 12. Accordingly, as cutting blade 12 is advanced in direction D with respect to cutting guide 20 (by advancing pivot 14 of moveable member 10 in direction D), the novel shape of hole 20 will cause cutting blade 12 to cut a preferred shape of cut in the cornea.

This can be seen as follows. Referring to FIG. 3, moveable member 10 is rotated in direction R about pivot 14 to the position shown in dotted lines as 10A. At such location, cutting guide restraint reaches the position shown in dotted lines as 16A (at which time it contacts the side of hole 22, as shown). Blade 12 is thus not able to rotate further in direction R than to the position shown in dotted lines as 12A. Thereafter, moveable member 10 will be rotated in the opposite direction such that cutting guide restraint 16 will instead contact the opposite side of hole 22 (thus limiting maximum angular movement in the opposite direction).

Concurrently, moveable member 10 will be moved in direction D with respect to cutting guide 20. This movement is shown by referring first to FIG. 4 and then to FIG. 2. (FIG. 4 shows the position of the moveable member with respect to the cutting guide when cutting is first commenced, and FIG. 2 shows the position of the moveable member with respect to the cutting guide after cutting has been carried out for some time.)

Figure 5A:
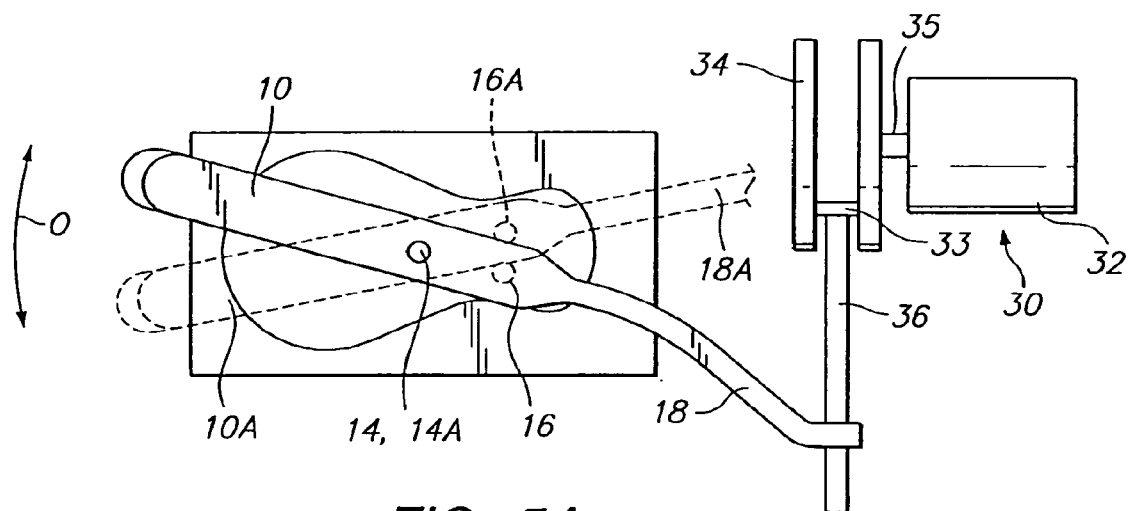
FIG. 5A is a top plan view showing the moveable member moved from a first position at which the cutting guide restraint contacts one side of the cutting guide (shown in solid lines) to a second position at which the cutting guide restraint contacts the other side of the cutting guide (showing in dotted lines).

FIG. 5A illustrates a mechanical system for oscillating moveable member 10 back and forth in direction O. Specifically, FIG. 5A shows moveable member 10 at a first maximum angular extension (shown in solid lines) and moveable member 10 at an opposite maximum angular extension (shown in dotted lines). In preferred aspects of the invention, moveable member 10 includes a flexible portion 18. Flexible portion 18 may optionally comprise a spring or a flexible piece of plastic or rubber. As can be seen, an advantage of having portion 18 flexible is that it bends when cutting guide restraint 16 is stopped from further angular movement by its contact with the sides of hole 22. A system 30 for oscillating moveable member 10 may include a motorized mechanical linkage for rotating moveable member 10 back and forth by alternatingly moving flexible portion 18 back and forth in a direction generally perpendicular to direction D. For example, system 30 may include a motor 32 that rotates a wheel 34 (by rotating shaft 35). A pin 33 is eccentrically mounted to wheel 34 such that as wheel 34 rotates, the movement of pin 33 causes link 36 to move back and forth, thereby repetitively moving moveable member 10 back and forth between positions (shown as 10 and 10A).

Figure 5B:
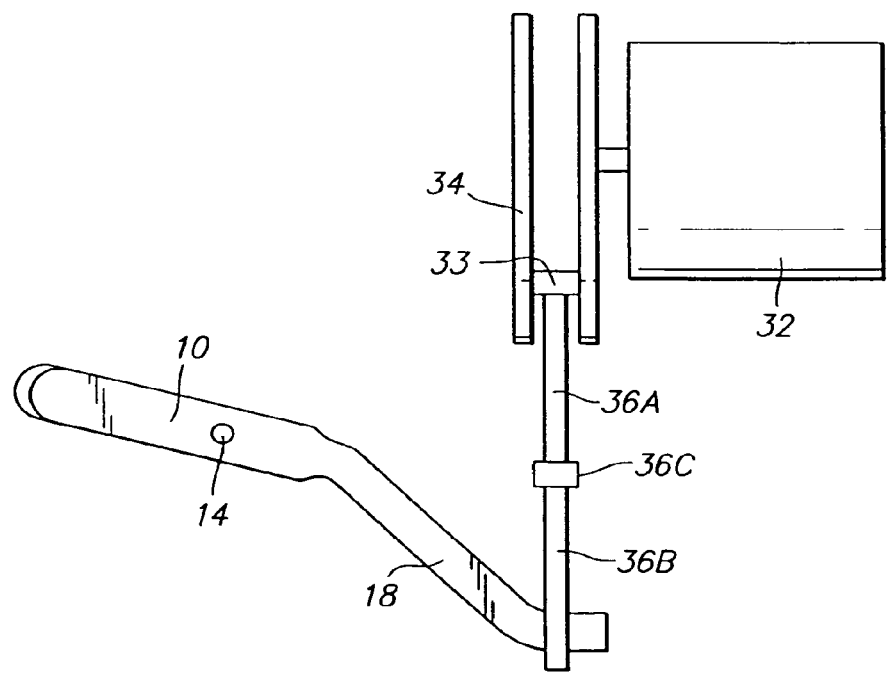
FIG. 5B is a top plan view showing the linkage of the moveable member to a motor as consisting of two links connected by a joint.
Figure 5C:
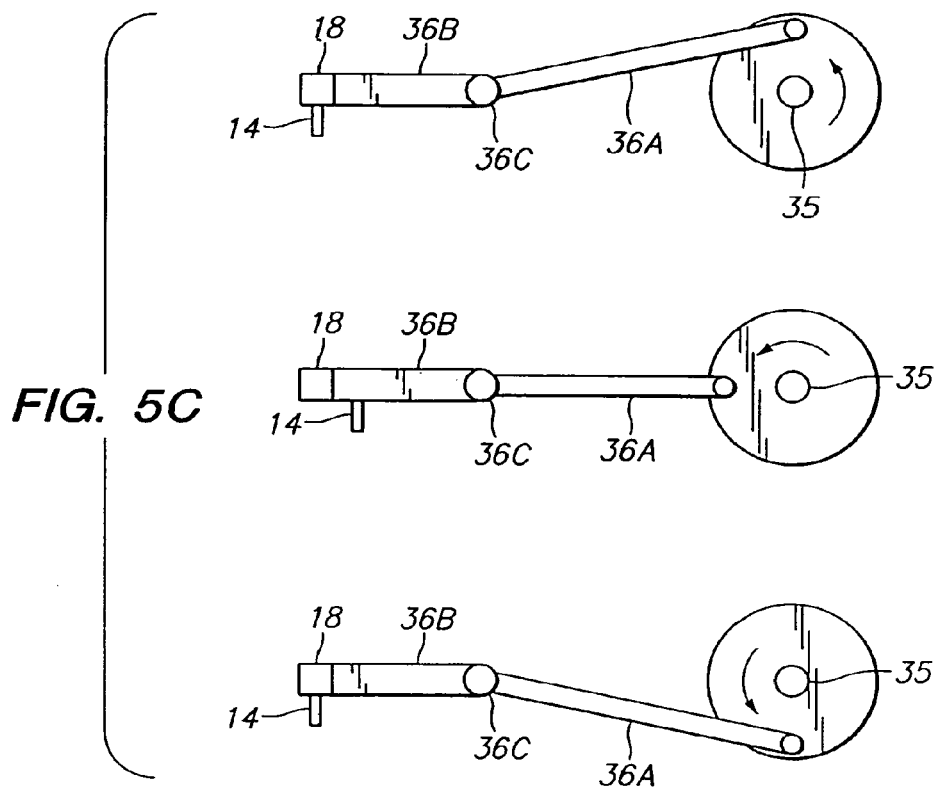
FIG. 5C is a schematic side elevation view showing that the presence of two sequential links connected by a joint can minimize vertical up and down motion of the moveable member.

In preferred aspects, link 36 may include more than one link member connected together in series. An advantage of having link 36 include more than one link member is that this can minimize up and down movement of the flexible portion 18 and moveable member 10 as pin 33 moves around shaft 35. FIG. 5B shows link 36 consisting of portions 36A, 36B, and 36C. Portion 36C is a joint which connects portion 36A and 36B. FIG. 5C shows how joint 36C allows portion 36A to move in a vertical up and down motion while portion 36B moves predominantly in a transverse horizontal motion relative to pivot 14. Portion 36B, therefore transmits predominantly horizontal back and forth motion to flexible portion 18 and moveable member 10 around pivot 14 and minimizes up and down motion.

As can be seen in FIGS. 1, 3 and 5, hole 22 in cutting guide has a novel shape. In particular, hole 22 has a "gourd" or a "bowling pin" shape. The present inventor has determined that such "gourd" or a "bowling pin" shaped hole will result in a corneal cut that is roughly shaped like an "ice cream cone" (i.e. a triangular section with a convexly-curved end). Preferably, hole 22 will have a symmetrical shape. As will be shown, a particular advantage of this shape of cut is that it will create a pocket in the cornea wherein the opening through the surface of the cornea is smaller in width than the internal dimensions of the pocket.

In accordance with the present invention, an applanating plate is positioned against the front surface the cornea and the intraocular pressure is elevated by a suction ring during the time the cornea is cut by the movement of the cutting blade. The applanating plate presses down against the front surface of the cornea and the intraocular pressure presses up against the back surface of the cornea, thereby uniformly flattening a portion of the cornea. This has the advantage of ensuring a uniform thickness of the cornea is cut by the cutting blade when forming a pocket, flap, or cap.

Figure 6A:
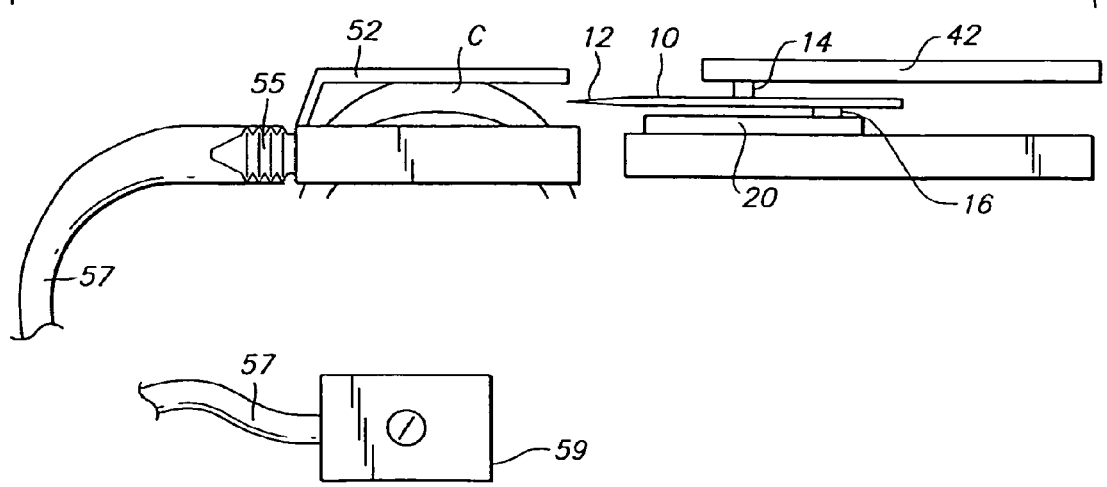
FIG. 6A is a schematic side elevation view of an embodiment of the invention in which a non-moving applanating plate flattens the surface of the cornea prior to cutting.
Figure 6B:
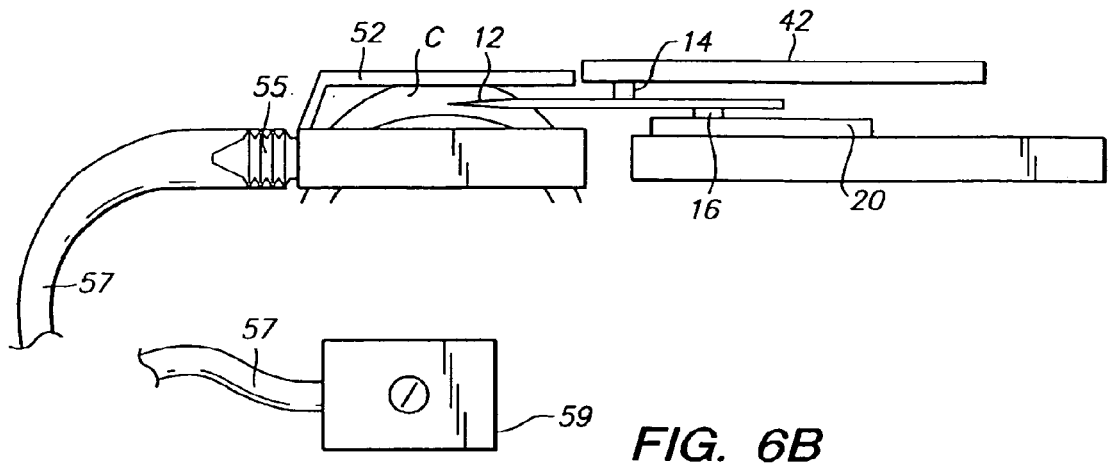
FIG. 6B is a schematic side elevation view of an embodiment of the invention in which a non-moving applanating plate flattens the surface of the cornea during cutting.
Figure 7A:
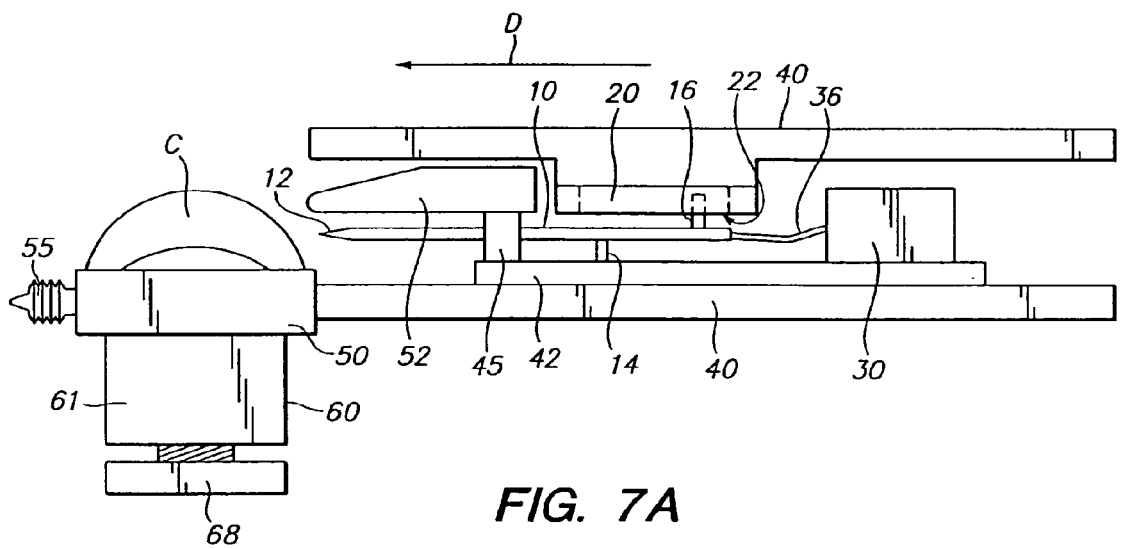
FIGS. 7A and 7B are sequential schematic side elevation views of an embodiment of the invention in which an applanating plate advances across the surface of the cornea simultaneously with the cutting blade cutting through the cornea.
Figure 7B:
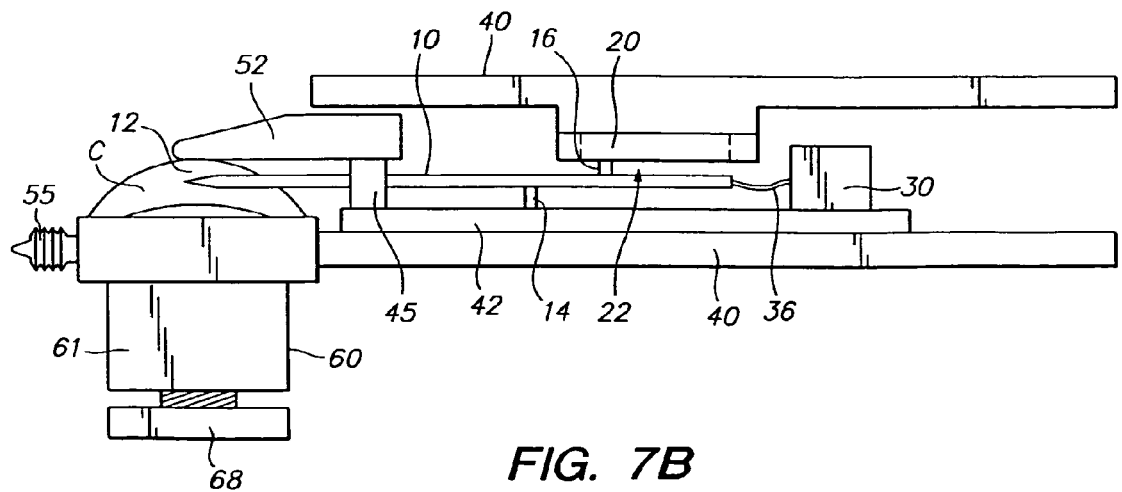
Figure 7C:
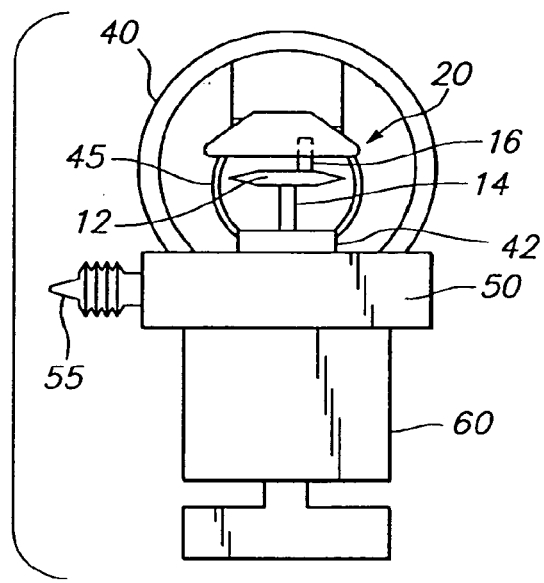
FIG. 7C is a front elevation view of the embodiment of the invention shown in FIGS. 7A and 7B.

In one embodiment, the applanating plate is positioned at a fixed location on the surface of the cornea prior to commencing cutting of the cornea with the cutting blade. An example of such system is shown in FIGS. 6A and 6B. In an alternate embodiment of the invention, the applanating plate is advanced over the surface of the cornea concurrently with the cutting blade penetrating and cutting across the cornea. An example of such system is shown in FIGS. 7A to 7C. Additionally, FIGS. 7A to 7C show an optional anterior chamber maintainer 60 which is especially useful when cutting a donor cornea. It is to be understood that anterior chamber maintainer 60 is an optional attachment that may or may not be used with the various embodiments of the invention shown in FIGS. 6A to 7C, as desired.

Referring first to FIG. 6A, when vacuum pump 59 connected to suction ring 50 by tubing 57 via tubing connector 55, creates a vacuum to a predetermined level, suction ring 50 holds cornea C (positioned therearound) in a fixed position. The vacuum transmitted by suction ring 50 also raises the pressure against the rearward surface of cornea C because the vacuum causes the eyeball to partially squeeze into the suction ring. The applanating plate 52 pushes down against the front surface of the cornea, thereby flattening the cornea. As illustrated, a member 42 is used to advance pivot 14 in direction D from the position shown in FIG. 6A to the position shown in FIG. 6B. (The relative movement of cutting guide restraint 16 within cutting guide 20 can be seen.) In accordance with the present invention, member 42 may include any form of mechanical linkage, guide rails or even simply a portion of the housing of the device.

FIGS. 7A to 7C show an alternate embodiment of the invention in which applanating plate 52 is moved across cornea C concurrently with blade 12 advancing (i.e. cutting through the cornea) in direction D. Moveable member 10, cutting guide 20 and system 30 are all positioned inside housing 40. As was explained above, system 30 causes moveable member 10 to rotate back and forth around pivot 14, with cutting guide restraint 16 is received within cutting guide 20. (In contrast to the embodiment of FIGS. 6A and 6B; however, pivot 14 instead projects from the bottom of moveable member 10, and cutting guide 20 is positioned above moveable member 10.) Member 42 is advanced in direction D within housing 40, thereby moving moveable member 10 in direction D. Cutting guide 20 is connected to housing 40 such that cutting guide restraint 16 moves along through hole 22 therein. Further details can be seen in FIG. 7C in which supports 45 hold applanating plate 52 within housing 40 such that moveable member 10 is free to move side-to-side therebetween.

FIGS. 7A and 7B show an optional anterior chamber maintainer 60 that may be used as an attachment to the present invention. Further details of the anterior chamber maintainer 60 are shown in FIGS. 8A and 8B. Anterior chamber maintainer 60 is specifically used when cutting tissue in a donor cornea. The donor corneal tissue is usually provided to the surgeon in the form of an excised cornea with a small rim of surrounding scleral tissue. As stated above, the present invention is designed to cut the cornea of a living complete eyeball. However, it is also necessary to have an attachment that will also enable the invention to cut a donated cornea that has been excised from the donor eyeball.

In accordance with the present invention, an optional anterior chamber maintainer 60 is provided to hold a donor cornea stable after the donor cornea has been cut away from the donor eyeball. As shown in the exploded view of FIGS. 8A and 8B, a cut away donor cornea C is placed on top of anterior chamber maintainer 60. In this preferred embodiment, suction ring 50 has an inner threading 63. The body of the anterior chamber maintainer 61 has an outer threading 62. The outer threading 62 is received into the inner threading 63 of suction ring 50. The inner threading 63 of suction ring 50 connects to outer threading of body 61, thereby firmly holding cornea C in place by trapping cornea C between suction ring 50 and body 61. The front surface of the cornea protrudes through the opening 51 of the suction ring. The body 61 has an interior chamber 66 that is filled with fluid or gas. A bottom portion 68 screws into the bottom end of interior chamber 66. By rotating bottom portion 68, the volume of interior chamber 66 can be adjusted. The top end 69 of fluid chamber 66 is open such that the fluid or gas within interior chamber 66 provides pressure against the rear surface of the donor cornea C. By providing pressure against the rear surface of donor cornea C, anterior chamber maintainer 60 simulates the pressures that would exist behind cornea C in a living eyeball. Moreover, the pressures produced in interior chamber 66 applied to the rear surface of cornea C allows the donor corneal tissue to be pressed flat against applanating plate 52 so that a cut of uniform depth can be made by blade 12. The amount of pressure inside the interior chamber may be measured by a pressure gauge or sensor connected to opening 67.

FIGS. 8A and 8B illustrate the tubing connector 55 on the top surface of the suction ring 50. This is an alternate location for tubing connector 55. In FIGS. 6A, 6B, 7A, 7B, and 9 the tubing connector 55 is shown on the side surface of the suction ring 50. FIG. 8B illustrates that there is a hollow space 56 inside tubing connector 55 which communicates with the inside of suction ring 50 that allows the vacuum pump 59 to generate vacuum inside suction ring 50. Advantageously, the generation of vacuum by vacuum pump 59 is not necessary for a cut to be made in the donor cornea C, because the cornea is already fixed in position by the anterior chamber maintainer 60 and the pressure on the rear surface of the cornea can also be sufficiently elevated by the anterior chamber maintainer 60.

Figure 9:
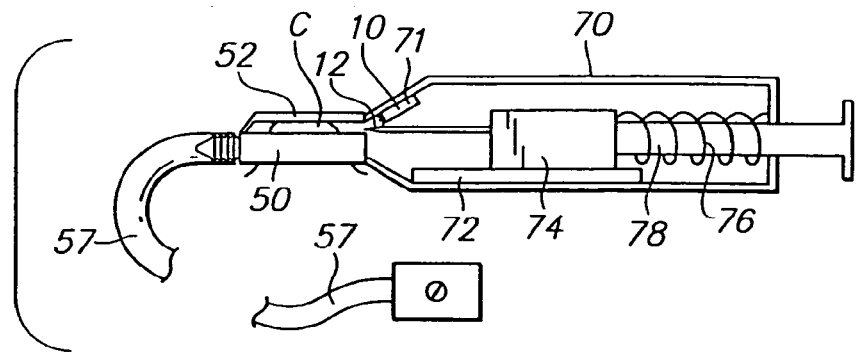
FIG. 9 is a sectional side elevation view of an embodiment of the invention in which an operator manually depresses a plunger to advance the cutting blade.

FIG. 9 shows another embodiment of the present invention in which the cutting blade is manually advanced by an operator. Within housing 70 are provided a guide rail or track 72 along which a cutting mechanism 74 moves. Cutting mechanism 74 may be a self-contained unit that includes moveable member 10, cutting guide restraint 16, a system for oscillating moveable member 10 about a pivot 14 thereon. A plunger 78 is connected to cutting mechanism 74. A spring 76 is connected at one end to housing 70 and at the other end to cutting mechanism 74. Spring 76 is a tension spring that tends to move cutting mechanism 74 so that blade 12 is retracted (as shown). When the operator depresses plunger 78, spring 76 will lengthen, and cutting mechanism 74 will move forward along track 72 such that blade 12 on moveable member 10 will advance between applanating plate 52 and suction ring 50, cutting through the cornea C. The interaction of cutting guide restraint 16 and cutting guide 20 will cause the cut to be of a preferred shape as was described above. Spring 76 will provide resistance to the forward motion of cutting mechanism 74 along track 72, thus, limiting uncontrolled forward motion of moveable member 10's cutting blade 12. Optionally, a liquid dispensing system 71 to spray fluid to cool the cutting blade and the cornea during cutting. Such a liquid dispensing system may be incorporated into any of the various other embodiments of the invention, as desired.

Figure 10:
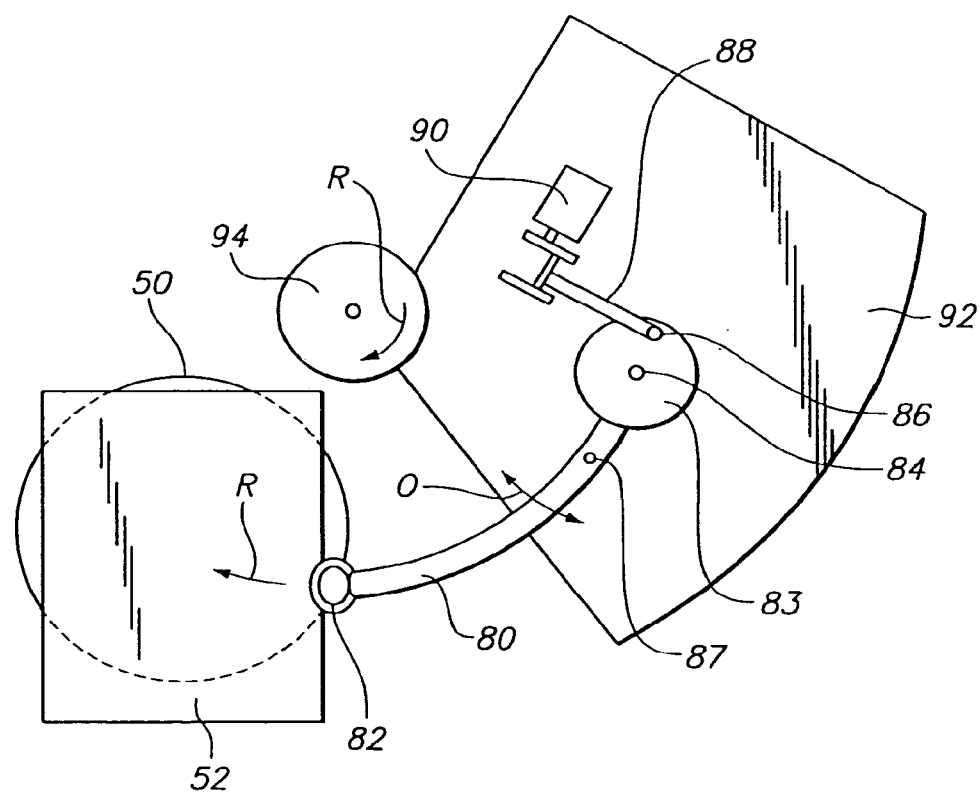
FIG. 10 is a top plan view of an embodiment of the invention in which the cutting blade is advanced through a curved path into the cornea.

FIG. 10 illustrates yet another embodiment of the invention in which a blade holder 80 having a blade 82 at one end is connected to moveable member 83 which pivots about a pivot point 84. As shown herein, blade 82 may be wider than the bladeholder 80, if desired. (Similarly, blade 12 may be wider than moveable member 10 in FIG. 1, if desired.) A motor 90 moves a linkage 88 back and forth. Linkage 88 is connected to moveable member 83 by flexible member 86 such that moveable member 83 is made to oscillate back and forth about pivot point 84. Thus, blade holder 80 and blade 82 oscillates back and forth in direction O. Blade holder 80 has a cutting guide restraint 87 disposed thereon. Cutting guide restraint 87 mates with a cutting guide (not shown) the shape of which limits maximum angular movement of blade 82, in the manner previously described above. The various components of the invention are mounted to a plate 92 that is connected to a rotatable member 94 that is rotated in direction R such that plate 92 is moved in direction R such that blade 82 and blade holder 80 will advance between applanating plate 52 (thereabove) and suction ring 50 (therebelow) to cut the flattened cornea.

As illustrated in various figures herein, pivot 14 and cutting guide restraint 16 may each comprise protrusions extending from moveable member 10. Moreover, in various figures herein, cutting guide 20 is illustrated as comprising a hole 22. The present invention is not so limited. For example, the pivot 14 on moveable member 10 may instead comprise a hole dimensioned to receive a protrusion therein. Moreover, the cutting guide restraint may instead comprise a slot with the cutting guide comprising some form of protrusion interacting therewith.

As stated above, the present invention may be used to for cutting a cornea on a living patient, or for cutting a donor cornea. Due to the accuracy of the present invention's system of cutting, the present invention may be used for removing diseased or damaged sections of a living patient's cornea, and then replacing these sections with similar shaped sections cut from a donor cornea.

In various aspects of performing the method of the present invention, the "section" of the cornea that is transplanted may be the front portion or the rear portion of the cornea. Cutting away a section of the front of the cornea and replacing the excised section with a donor graft is known as "anterior lamellar keratoplasty". Cutting away a section of the rear of the cornea and replacing the excised section with a donor graft is known as "posterior lamellar keratoplasty".

FIG. 11 illustrates an anterior lamellar keratoplasty procedure performed with prior art techniques; and FIG. 12 illustrates an anterior lamellar keratoplasty procedure performed with a technique in accordance with the present invention. FIG. 13 illustrates an posterior keratoplasty procedure performed with prior art techniques; and FIG. 14 illustrates a posterior lamellar keratoplasty procedure performed with a technique in accordance with the present invention. In each of FIGS. 11 to 14, a cut passing through the exterior of the cornea is shown in solid lines and a cut passing only through the interior of the cornea is shown in dotted lines.

Turning first to FIG. 11, a standard anterior lamellar keratoplasty procedure is shown. Specifically, a cut 100 is made through cornea C such that a frontal "cap" CA of tissue is removed for transplantation. A disadvantage of transplanting a frontal cap CA formed by cut 100 is that it s rather fragile, and prone to dislocation after surgery.

By instead using the present invention to form a cut 102 (FIG. 12), a pocket can be made in the cornea. A particular advantage of forming a pocket by cut 102 is that the pocket will have an opening 103 that is smaller than the interior width of the pocket. After the cutting blade forms cut 102, a trephine can be used to cut straight downwards into cornea in a cylindrical shaped cut 104. When cut 104 reaches cut 102, a cylindrical shaped portion CY of the cornea will be formed. This cylindrical shaped portion CY of the cornea of the donor cornea can then be transplanted into a similar cylindrical shaped hole cut into the living patient's cornea. A particular advantage of transplanting such a cylindrical shaped section (as opposed to transplanting a simple cap CA as shown in FIG. 11) is that a cylindrical shaped cornea section received into a cylindrical shaped hole will be much more stable and resistant to injury. Specifically, the donated corneal tissue would be much less likely to dislocate with vertical or lateral pressure following transplantation. After healing, the donor recipient disk would be much more resistant to vertical and or lateral displacement from mild trauma than superficial corneal tissue transplanted without the physical support of a rim of surrounding recipient corneal tissue.

Turning to FIG. 13, a standard posterior lamellar keratoplasty procedure is shown. A cut 110 is made in cornea C, as shown. Cut 110 does not pass fully across the cornea. Rather, a flap F of corneal tissue is formed by cut 110. After flap F is pulled back, a trephine or trephine section is then used to cut straight downwards, thus cutting a circular shaped cut 112 forming a cylindrical shaped portion CYR of the rear of the cornea.

By instead using the present invention to form a cut 120, (FIG. 14) a pocket can be made in the cornea. A particular advantage of forming a pocket by cut 120 is that the pocket will have an opening 123 that is smaller than the interior width of the pocket. After the cutting blade forms cut 120, a thin profile trephine (preferably mounted on a ring) or microsurgical scissors can be used to cut straight downwards into the deep layers of the cornea in a cylindrical shaped cut 124, thus forming a cylindrical shaped portion CYR of the rear of the cornea. An advantage of performing the operation in this manner is that it is not necessary to form and pull back a "flap" of tissue from the front of the cornea. Instead, the entire operation is performed without a large portion of the cornea being "open" to the external environment. Rather, the only opening into the cornea is through opening 123. This dramatically reduces the possibility for suprachoroidal hemorrhages.

In preferred aspects of the resent invention, openings 103 or 123 have a width of about 4 or 5 mm and interior pockets 102 and 120 have a maximum internal diameter of about 9 or 10 mm. Cylindrical corneal sections CY and CYR typically are about 7 to 8 mm in diameter in the patient's eye, and about 7 to 8 mm in diameter in the donor cornea.

In various aspects, the portion CYR of the donor cornea can be completely excised with the use of microsurgical scalpels and or scissors, and portion CY can be manually separated from the superficial layers of the cornea using microsurgical forceps.

In various aspects, viscoelastic can be injected onto the inside surface (relative to the center of tine eyeball) of the CYR portion of the donor cornea to protect the corneal endothelium. The inner layer of the cornea is then partly folded in half with microsurgical forceps, with a cushion of viscoelastic preventing the endothelium on each half of the donor disk CYR from touching together. Viscoelastic can also be used to position the donor corneal disk into the space previously occupied by the excised recipient corneal disk CYR.

The opening 103 or 123 of the corneal pocket may optionally be closed with sutures or tissue glue to make the wound water tight. Possible tissue glues which could be used include cyanoacrylate, fibrinogen tissue adhesives, or dendrimers. Viscoelastic can be removed from the anterior chamber using irrigation of balanced salt solution and aspiration.

It is to be understood that the dimensions for the size and shape of cuts made in the recipient and donor corneal tissues are merely representative of the type of surgery which can be done. Thus, variations in the dimensions and shape of the pocket, flap, cap, and corneal donor or recipient disks are expected, all keeping within the scope of the present invention.

Figure 15A:
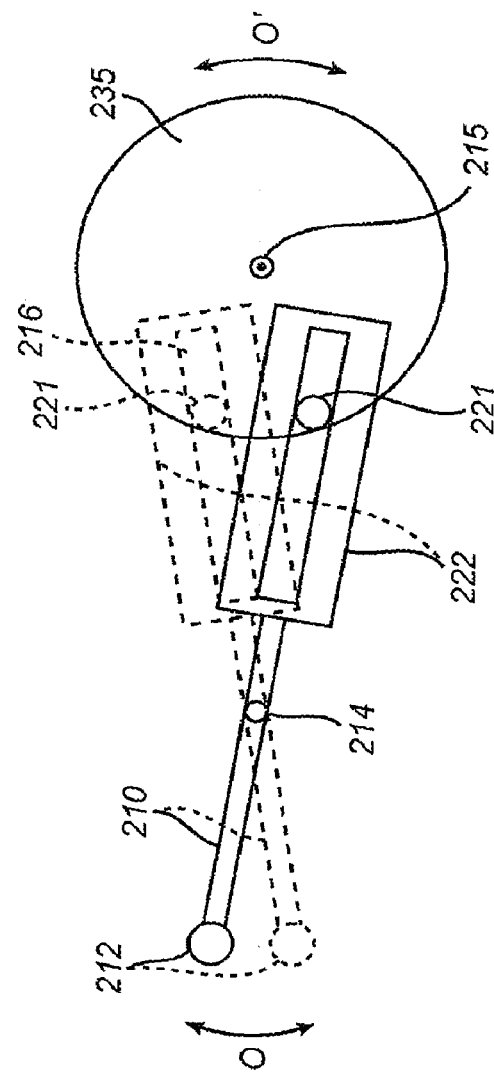
FIG. 15A is a top plan view of a mechanical system for moving a moveable member and cutting blade in accordance with the principles of the present invention.

Referring to FIG. 15A a top view of a mechanical system for oscillating moveable member 210 along non-linear path O around pivot element 214. Specifically, FIG. 15A shows moveable member 210 at a first position (shown in solid lines) and moveable member 210 in a second position (shown in dotted lines). Moveable member 210 is moved from the first position to the second position along a non-linear path O, by the movement of restraining element 221 within hollow slot 216 in a cutting guide restraint 222. Restraining element 221 in this embodiment is a protrusion, but in alternative embodiments may be a hole designed to receive a protrusion. In preferred aspects, restraining element 221 is mounted eccentrically on a wheel 235 which is connected to a programmable oscillating motor 232 (FIG. 15B) such as a stepper or servo motor. The programmable oscillating motor turns wheel 235 around pivot element 215 in direction O'. In this embodiment, the cutting guide comprises a software program which limits the angular motion of programmable oscillating motor 232. Programmable oscillating motor 232 is engaged to cutting guide restraint 216 by restraining element 221. The cutting guide software program thereby limits the degree of angular movement of cutting element 212 around pivot element 214. Cutting element 212 may be a solid cutting blade, but may also be any other cutting mechanism appropriate to cut the cornea e.g. electromagnetic energy such as a laser or plasma field. In alternate preferred aspects, cutting element 212 is deformable in shape and size, such as in the case of a sharp wire loop that can be extended or retracted to increase or decrease the cutting surface. The deformability of the blade advantageously allows the size of the blade to increase once it is beyond the entry incision which helps to enable the creation of a large pocket through a small incision.

Figure 15B:
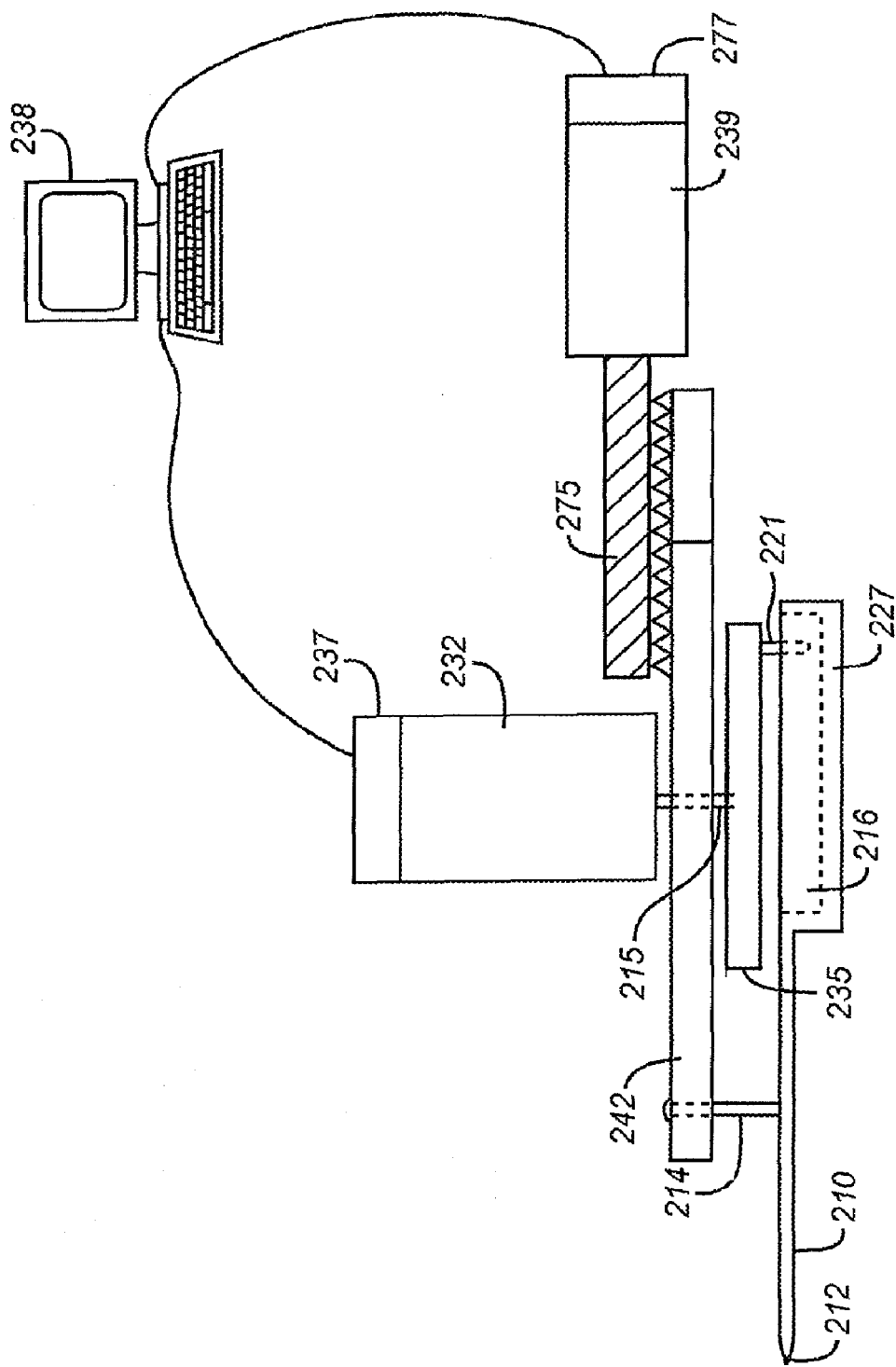
FIG. 15B is a side view of a system employing the mechanism of FIG. 15A.

FIG. 15B illustrates a side view of the above described mechanical system. Restraining element 221 is located within a hollow slot 216 (shown in dotted lines) of the cutting guide restraint 222. When programmable oscillating motor 232 turns wheel 235, moveable member 210 pivots around pivot element 214. In preferred aspects, the movements of the programmable oscillating motor are controlled by a cutting guide (software program) encoded within encoder 237 or computer 238. In one embodiment, the cutting mechanism including moveable arm 210, cutting element 212, pivot element 214, cutting guide restraint 216, wheel 234, and programmable oscillating motor 232 are all mounted on a platform 242. The cutting mechanism components can be driven forward by a programmable drive motor 239. In preferred aspects, when programmable drive motor 239 turns a lead screw 275 that is engaged to threads 244 on platform 242, the platform and the cutting mechanism will move forward or back. Alternative methods of moving the cutting mechanism forward and back (e.g. with motors, pneumatics, and the like) can also be used and are all within the scope of the described invention. In preferred aspects, movements of the programmable drive motor 239 are controlled by the cutting pattern guide software program that is encoded within encoder 237 and/or computer 238.

Figure 16:
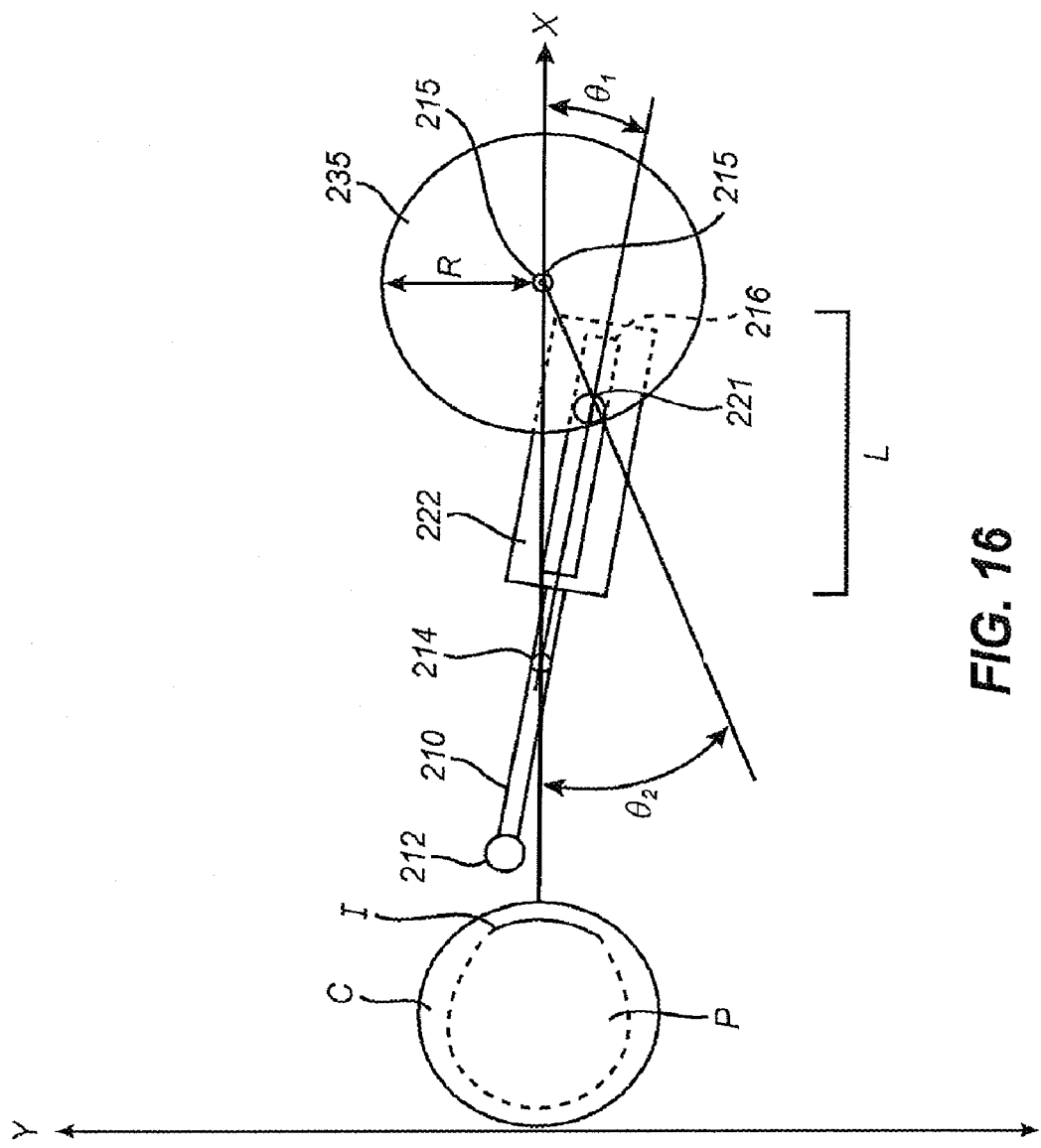
FIG. 16 illustrates an alternative mechanical system for manipulating a moveable member and cutting blade.

FIG. 16 illustrates an embodiment where the cutting pattern guide comprises a software program that controls the movements of a programmable oscillating motor (not shown) and a programmable drive motor (not shown). The programmable oscillating motor is connected to wheel 235. The angular movement $\theta_2$ of blade 212, moveable member 210, and cutting guide restraint 216 around pivot point 214 is controlled by the movement of restraining element 221 within hollow slot 216 of cutting guide restraint 222. Restraining element 221 is mounted on wheel 235 of radius R which rotates around center point 215. When wheel 235 rotates, an angle $\theta_1$ is formed between the X axis and the line through pivot point 215 and restraining element 221. The distance between pivot point 214 and center point 215 is L. Using trigonometry the relationship between an angle $\theta_2$ and $\theta_1$ can be determined. The cutting guide software program thereby controls the path of the cut into cornea C by controlling the rotation of wheel 235 through the programmable oscillating motor and the movement of the moveable member along the X-axis through the programmable drive motor. Please note, during the creation of the pocket P through incision I, cornea C is temporarily flattened by the use of an applanator (not shown). The cornea C may be part of a living eyeball or may be a donor cornea that has been excised from a cadaveric (donor) eyeball.

Figure 17:
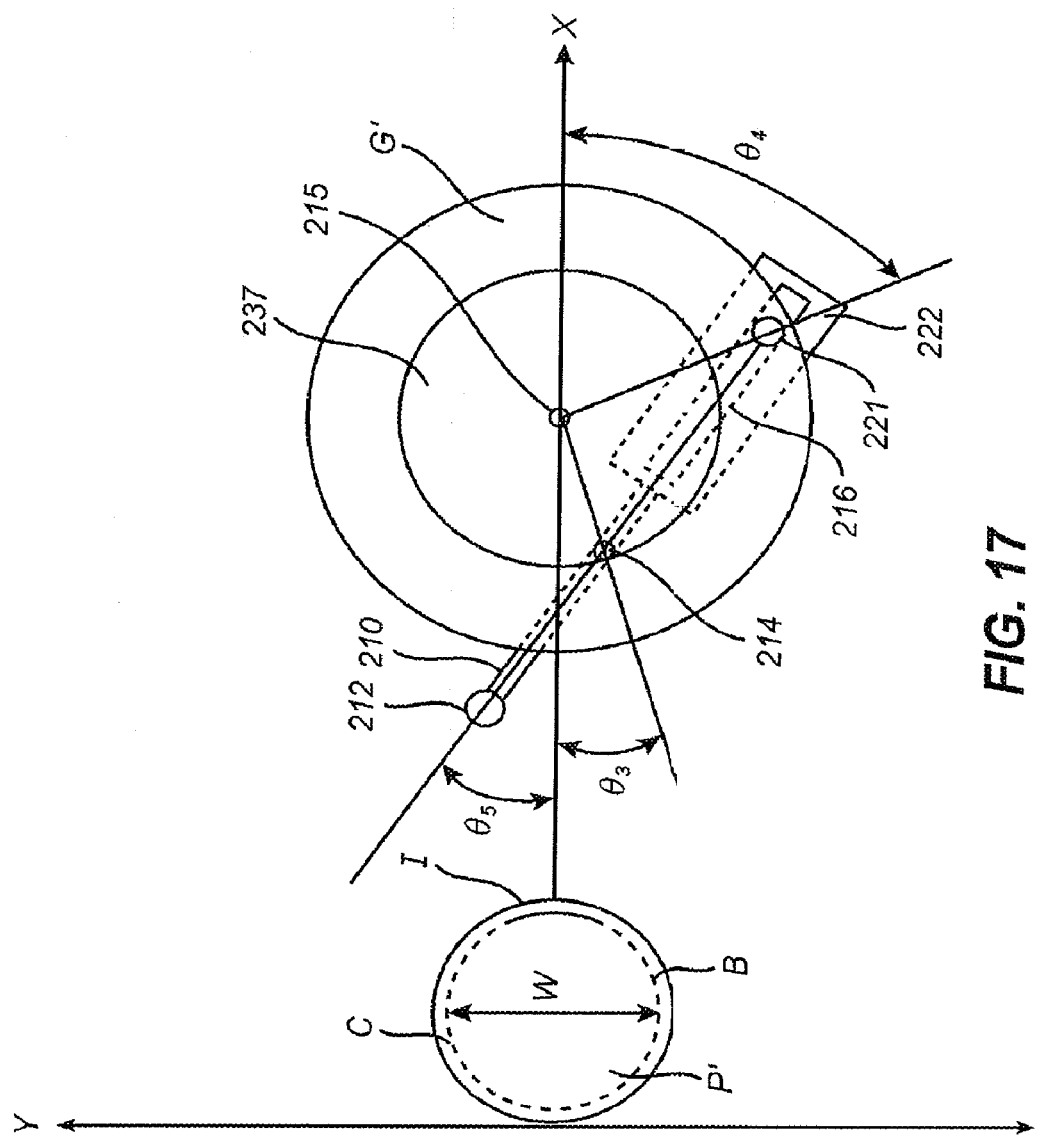
FIG. 17 illustrates a system where the moveable member is mounted on a pivot point which moves over a circular path.
Figure 18A:
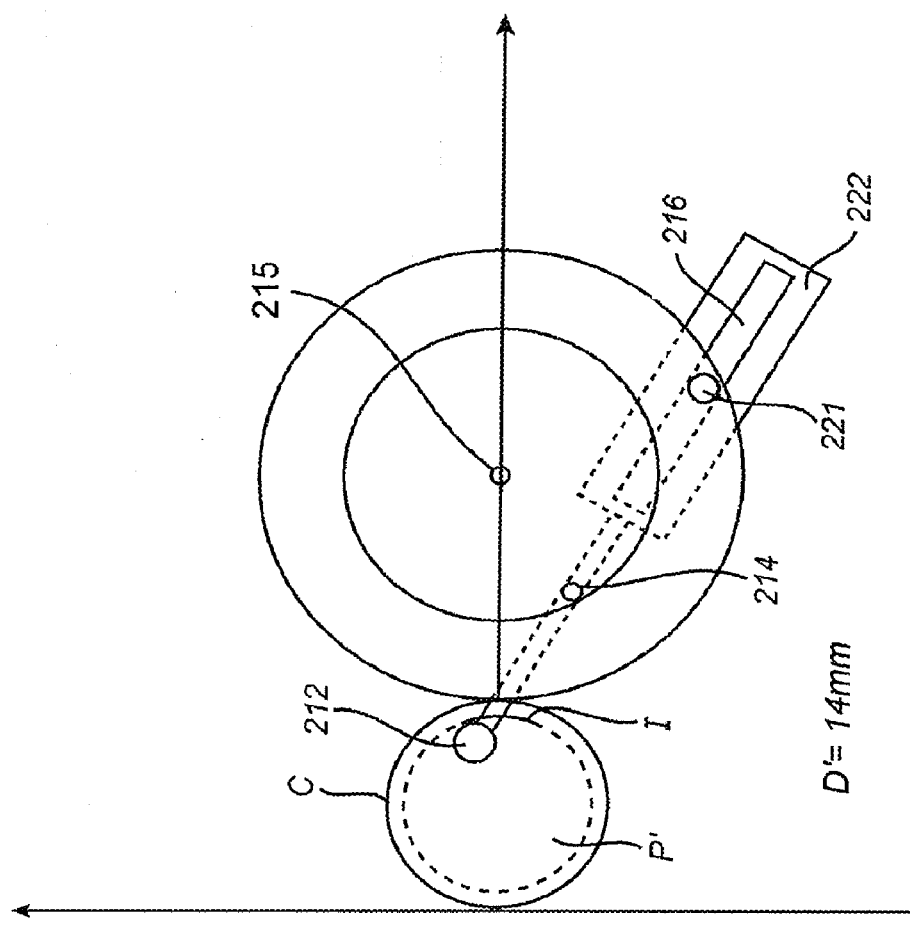
FIGS. 18A-18D provide an example of the motion of the cutting system of FIG. 17.
Figure 18B:
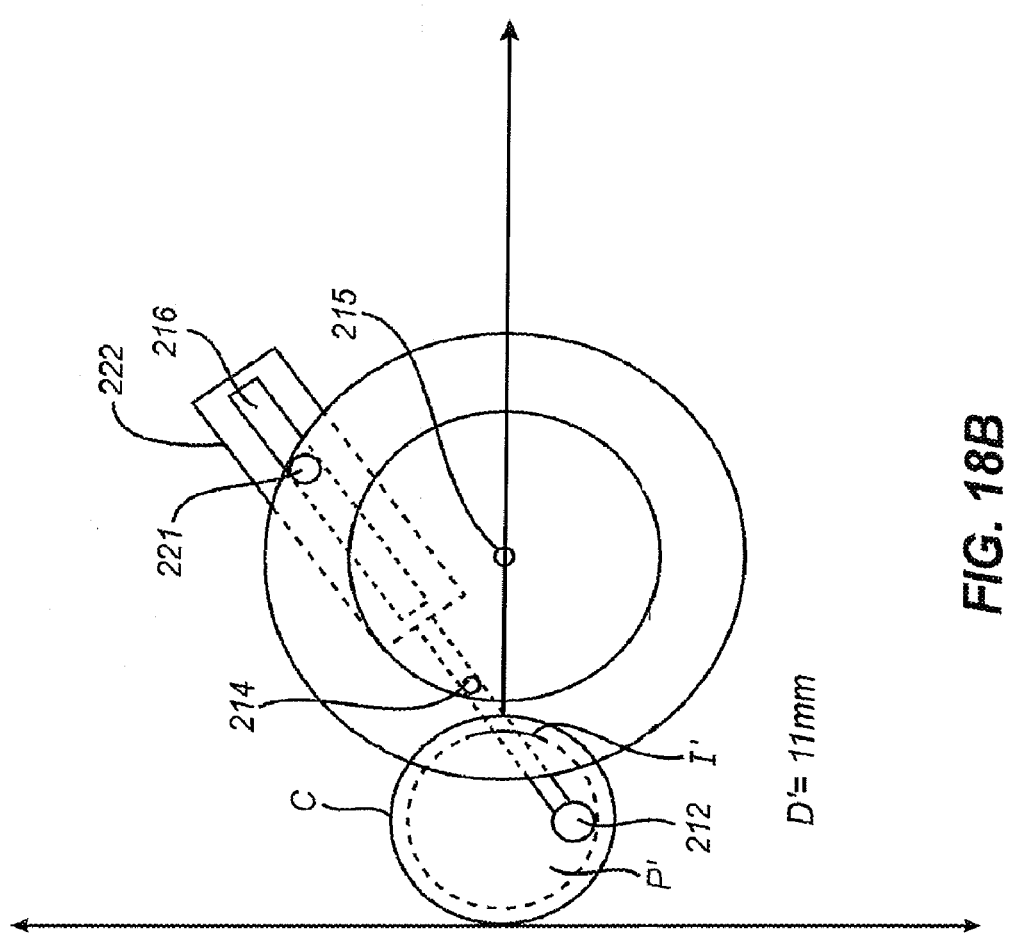
Figure 18C:
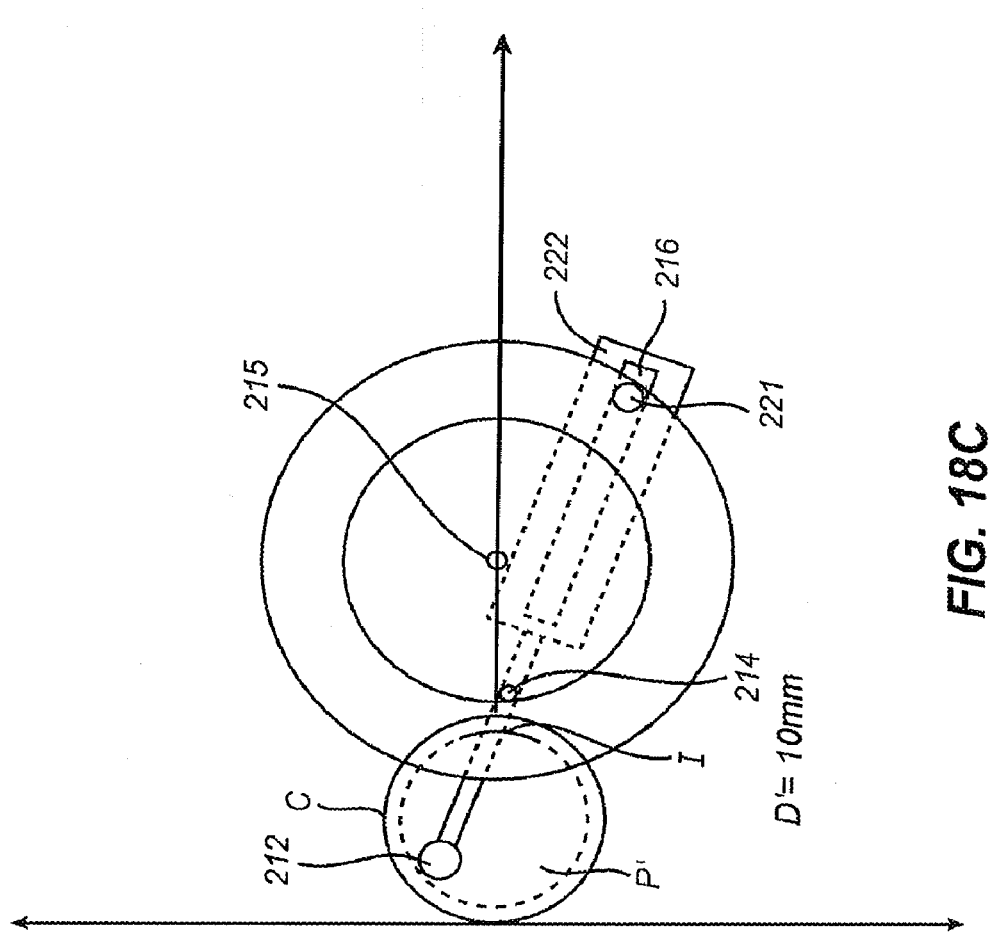
Figure 18D:
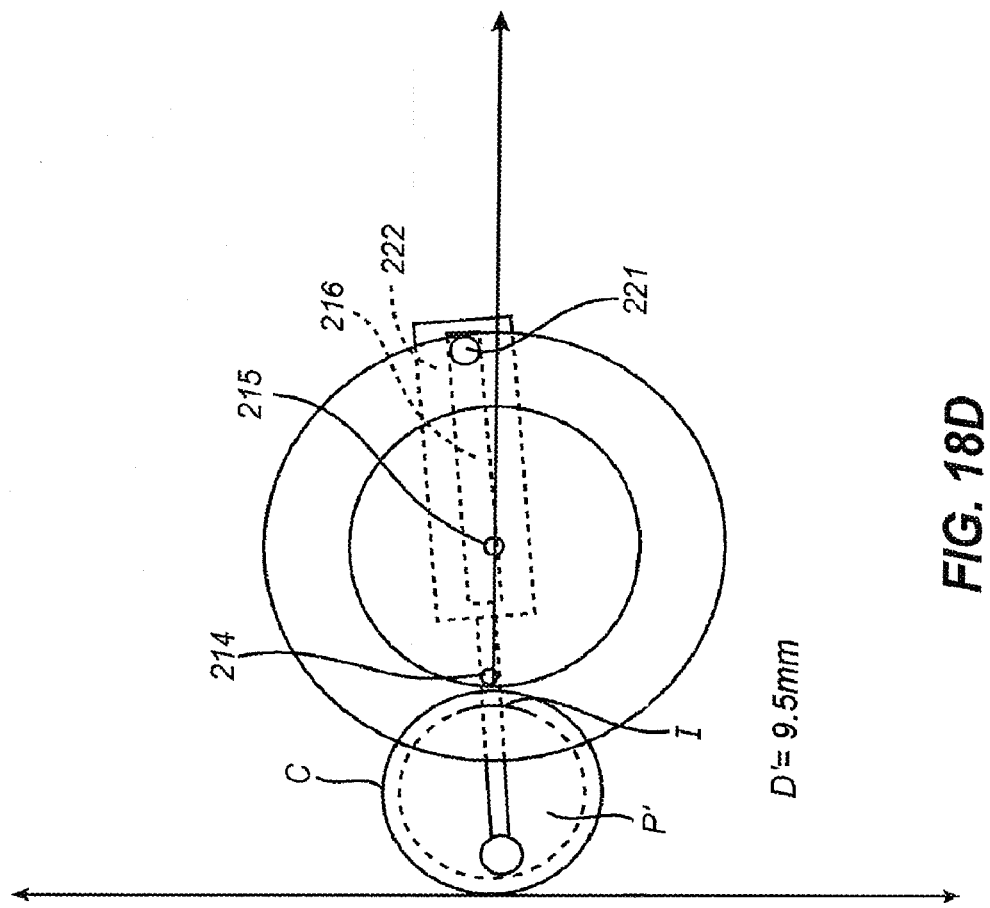

As shown in FIG. 17, if the position of pivot point 214 is adjustable in both the X axis and the Y axis, such additional freedom of movement allows the cutting element to create a relatively large pocket P' through a small external opening I. Specifically the maximal width W of pocket P' may be more than twice the width of incision I. The internal boundary B of Pocket P' is shown in dotted lines. In this FIG. 17, width of entry incision I is 4 mm and the maximum width W of pocket P' is 10 mm. This can be created with a 2 mm wide blade 12, with a moveable member 10 of 1 mm width, and a pivot element 214 which is 12 mm behind the tip of the cutting element 212.

In the embodiment of FIG. 17, the position of pivot point 214 is made adjustable by mounting pivot point 214 on a wheel 237. Wheel 237 turns around pivot point 215. Restraining element 221 is mounted on a gear G' and is located within hollow slot 216 cutting guide restraint 222. Gear G' is concentric to wheel 237 and is also centered on pivot 215. Moveable member 210 and cutting guide restraint 222 are shown in dotted lines to indicate that they are beneath wheel 37 and gear G'. Gear G' is rotated by a second gear (not shown) that is engaged to a programmable motor (not shown). The angles of the cutting element 212, moveable member 210, and cutting restraint 216 are determined by the relative positions of pivot point 214 and restraining element 221. The positions of pivot point 214 and restraining element 221 are determined by two separate programmable motors (not shown) which control the rotational angles of wheel 37 and gear G'. Angle $\theta_3$ represents the angle between the X-axis and the line drawn through pivot point 214 and center point 215 and the X axis. Angle $\theta_4$ represents the angle between the X-axis and the line drawn through restraining element 221 and center point 215. Angle $\theta_5$ represents the angle between the X-axis and the line drawn through restraining element 221 and pivot point 214. Angle $\theta_5$ also represents the angle between the cutting element 212 and the X axis. In order to create a pocket within the cornea, cutting element 212, moveable member 210, cutting restraint 222, wheel 237 are all moved toward cornea C along the X axis by a programmable drive motor (not shown), while the positions of the pivot point 214 and restraining element 221 are determined by programmable motors that are controlled by cutting guide software.

Table I shows a sample set of parameters for D', $\theta_5$, $\theta_3$, $\Theta_4$ that can be used to cut a pocket within the cornea which has a 4 mm entry incision I and an internal width W of 10 mm. The blade 12 is 2 mm wide with a moveable member 10 of 1 mm width, and a pivot element 14 which is 12 mm behind the tip of the cutting blade 12. Positive values indicate clockwise rotation from the X-axis. Negative values indicated counter-clockwise rotation from the X-axis. The following parameters can be incorporated into cutting guide software that controls programmable motors.

The cutting path derived from the parameters in Table I is shown in FIGS. 18A-18D. For each distance D' of pivot point 215 away from cornea C, the positions of blade 212, pivot element 214, and restraining element 221 are shown in relation to pocket P' and incision 1.

TABLE 1

| Distance of Center of Wheel from the Cornea D' | Angle of Blade in degrees $\theta_5$ | Angle of Pivot in degrees $\theta_3$ | Angle of Restraining Element in degrees $\theta_4$ |
|---|---|---|---|
| 19 | 0 | 0 | 0 |
| 19 | −5 | 0 | −9 |
| 19 | 0 | 0 | 0 |
| 19 | +5 | 0 | +9 |
| 18 | 0 | 0 | 0 |
| 18 | −5 | 0 | −9 |
| 18 | 0 | 0 | 0 |
| 18 | +5 | 0 | +9 |
| 17 | 0 | 0 | 0 |
| 17 | −5 | 0 | −9 |
| 17 | 0 | 0 | 0 |
| 17 | +5 | 0 | +9 |
| 16 | 0 | 0 | 0 |
| 16 | −5 | 0 | −9 |
| 16 | 0 | 0 | 0 |
| 16 | +5 | 0 | +9 |
| 15 | 0 | 0 | 0 |
| 15 | −5 | 0 | −9 |
| 15 | 0 | 0 | 0 |
| 15 | +5 | 0 | +9 |
| 14 | 0 | 0 | 0 |
| 14 | +30 | −34 | +65 |
| 14 | 0 | 0 | 0 |
| 14 | −30 | +34 | −65 |
| 13 | 0 | 0 | 0 |
| 13 | −30 | +24 | −71 |
| 13 | 0 | 0 | 0 |
| 13 | +30 | −24 | +71 |
| 12 | 0 | 0 | 0 |
| 12 | +37 | −22 | +73 |
| 12 | 0 | 0 | 0 |
| 12 | −37 | +22 | −73 |
| 11 | 0 | 0 | 0 |
| 11 | −35 | +18 | −68 |
| 11 | 0 | 0 | 0 |
| 11 | +35 | −18 | +68 |
| 10 | 0 | 0 | 0 |
| 10 | +20 | −8 | +39 |
| 10 | 0 | 0 | 0 |
| 10 | −20 | +8 | −39 |
| 9.5 | 0 | 0 | 0 |
| 9.5 | −5 | 0 | −9 |
| 9.5 | 0 | 0 | 0 |
| 9.5 | +5 | 0 | +9 |
| 9.5 | 0 | 0 | 0 |

Figure 19:
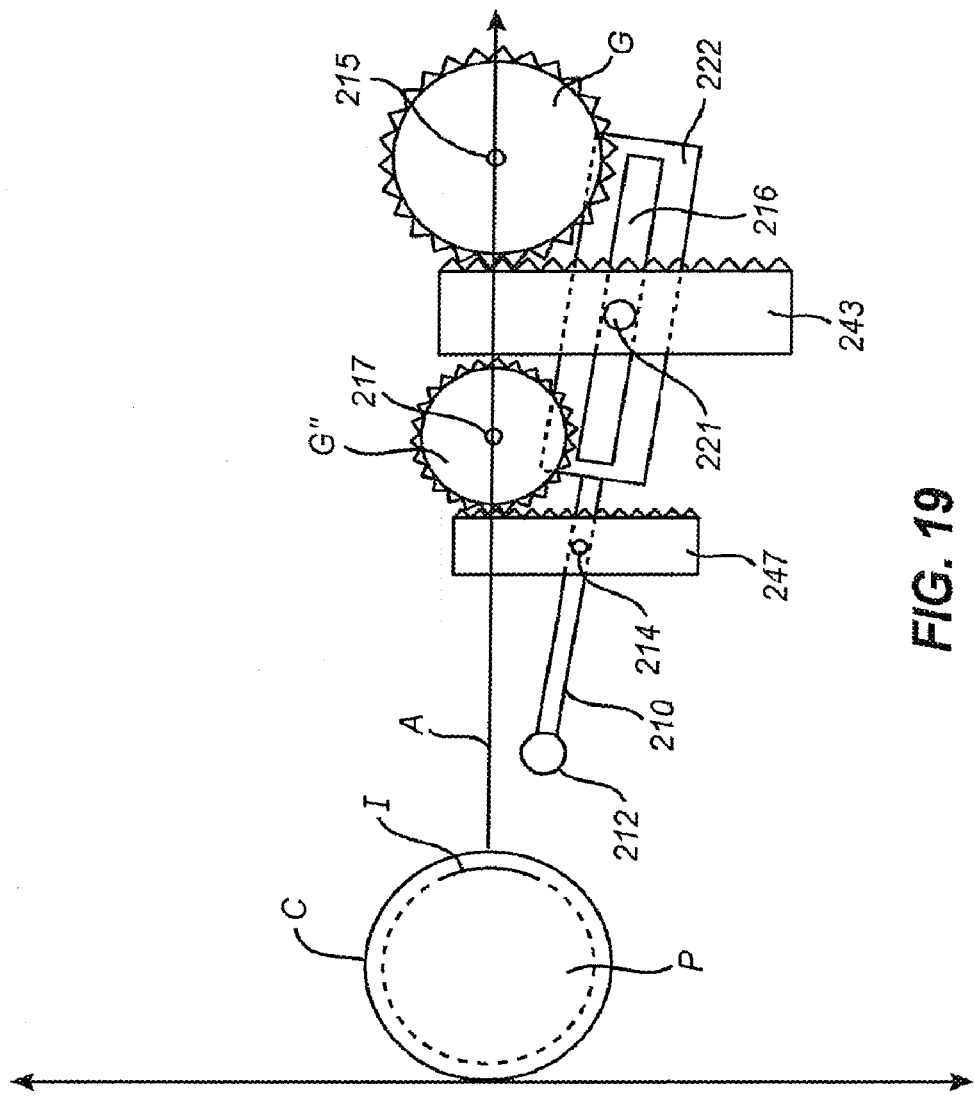
FIG. 19 is yet another embodiment of a mechanism for manipulating a moveable member and cutting blade in accordance with the principles of the present invention.
Figure 20A:
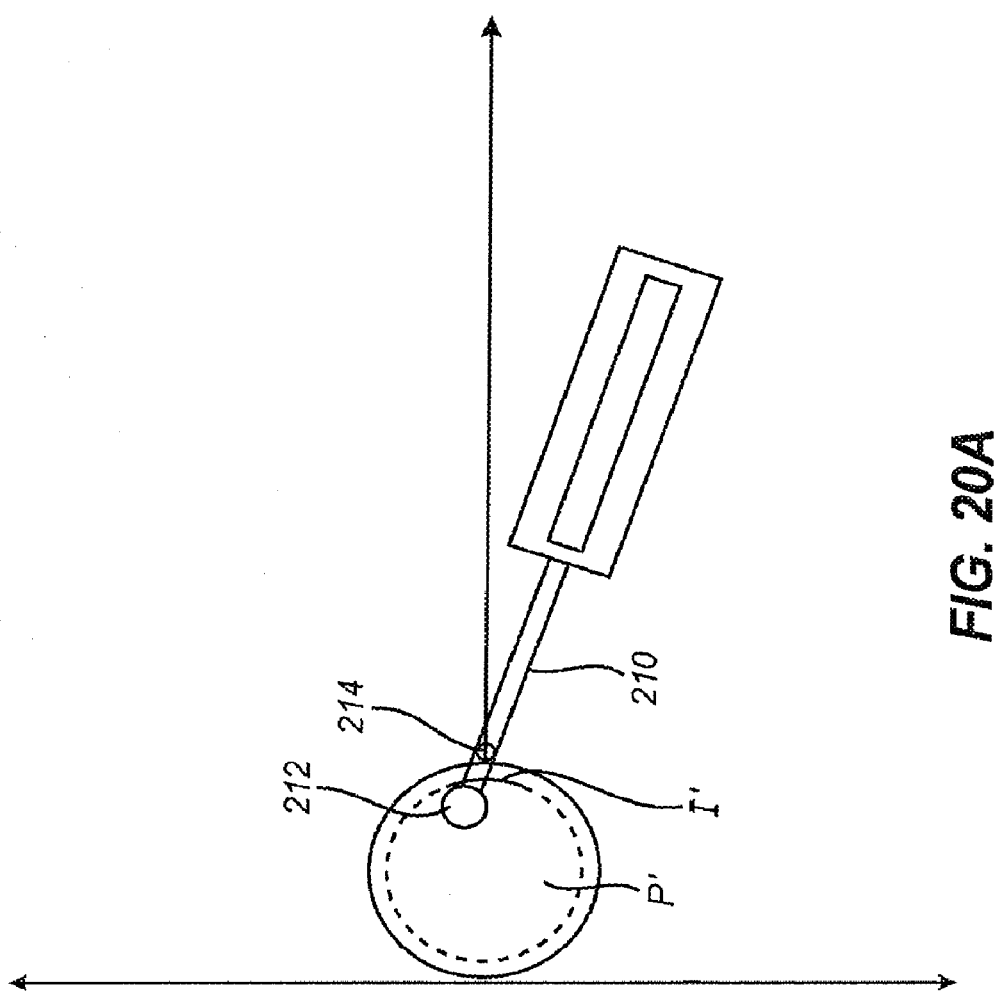
FIGS. 20A-20D illustrate how a large pocket can be made through a small incision over a fixed pivot point.
Figure 20B:
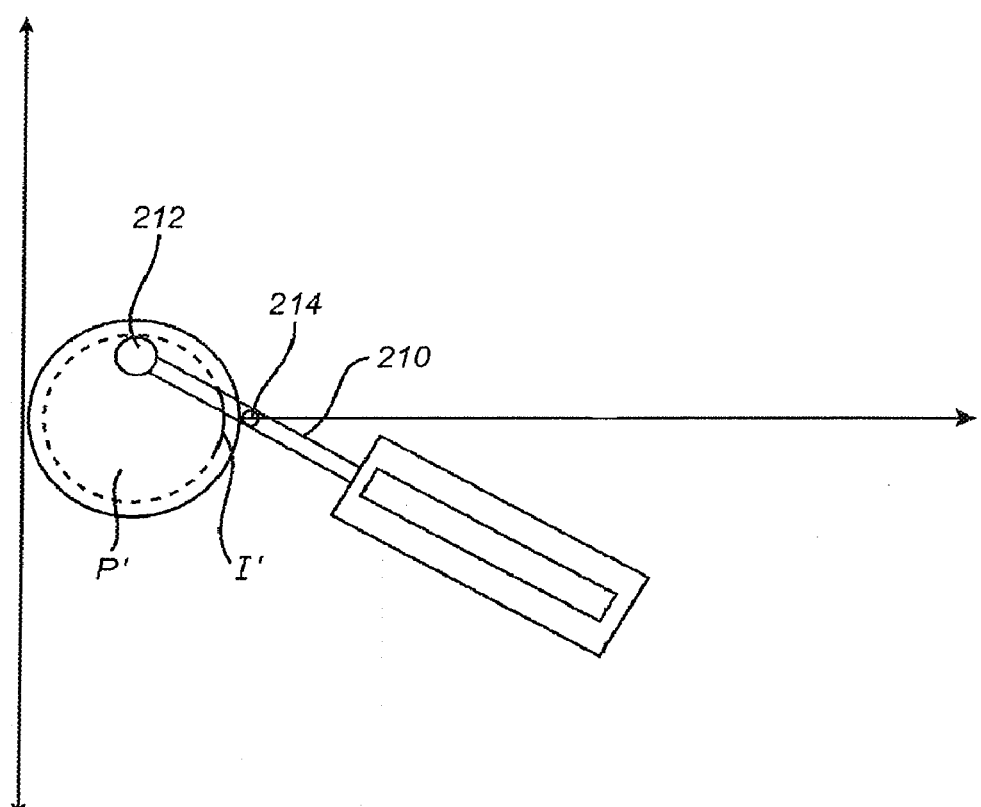
Figure 20C:
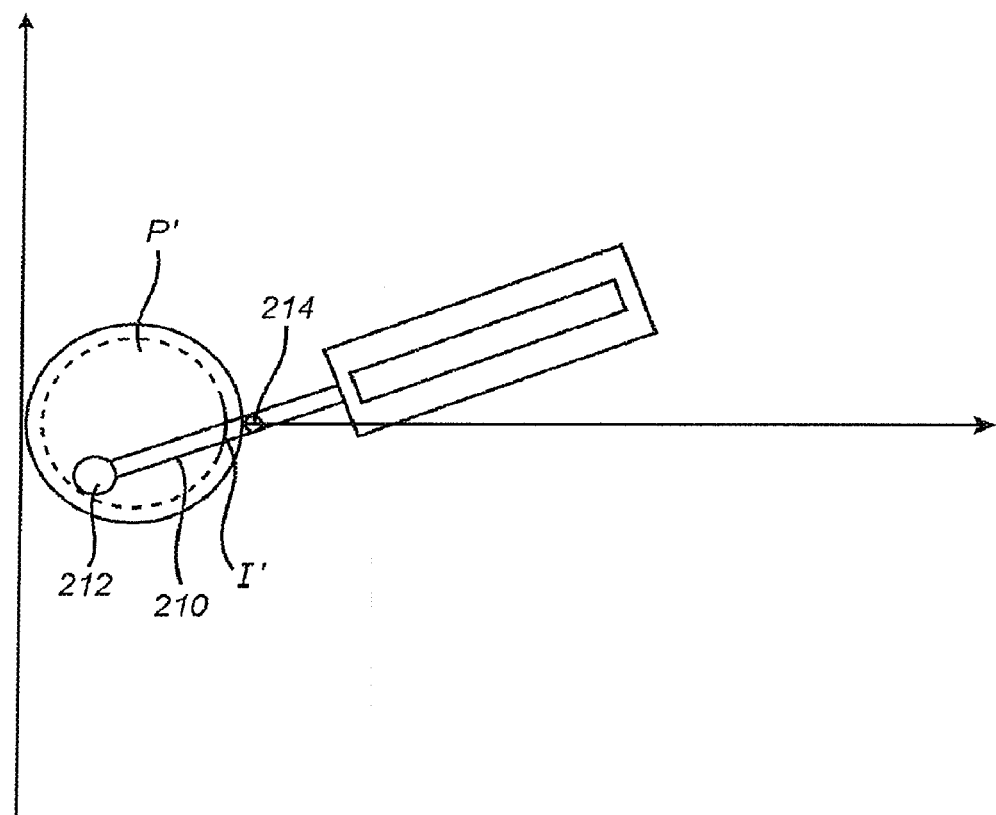
Figure 20D:
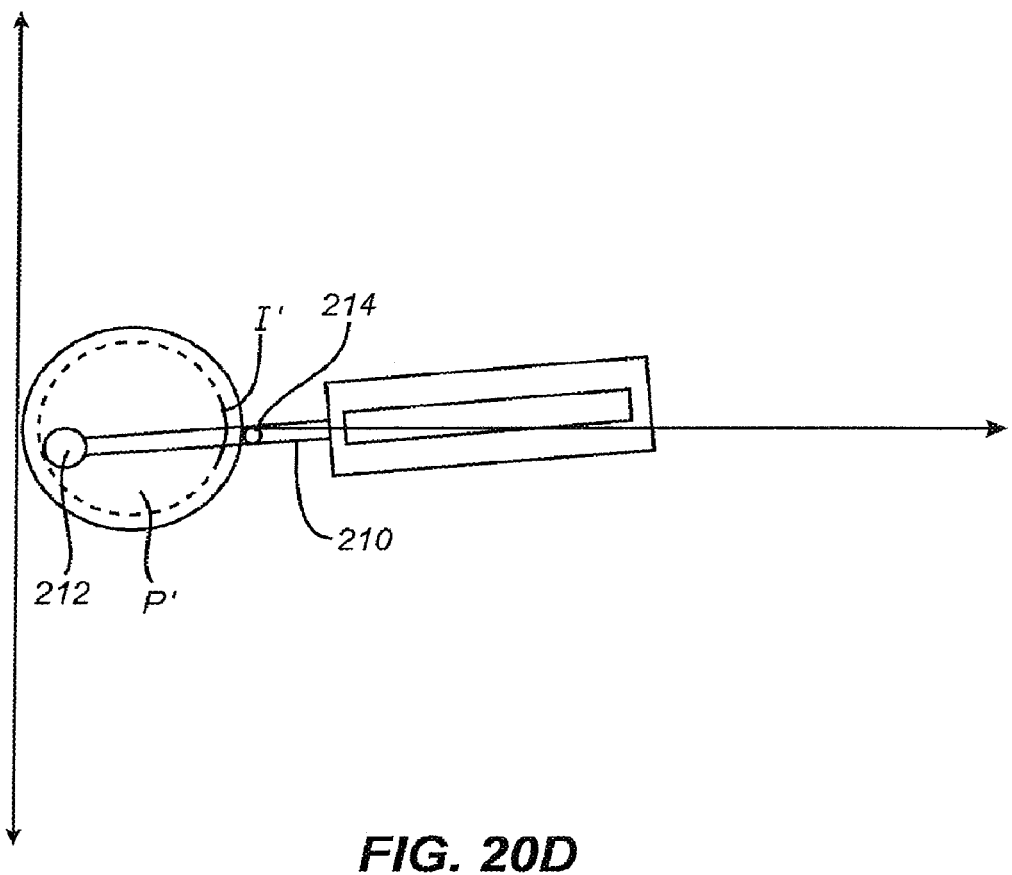

An alternative embodiment is shown in FIG. 19 where the pivot point 214 is mounted on a platform 247 and restraining element 221 is mounted on platform 243. Gear G rotates around center point 215 and gear G'' rotates around center point 217. The rotation of gears G and G'' determines the angle of blade 212 relative to axis A. Through the use of trigonometry, a table can be created and then used to program the cutting guide software to create a corneal pocket. Combinations of rotatable wheels and platforms that move along linear paths may also be used to position pivot point 214 and restraining element 221.

Another way that a relatively large pocket can be made through a small incision is to fixate pivot point 214 relative to the cornea, but to allow the moveable member 210 to translate and rotate over or under the pivot point 214. FIGS. 20A-20D show the moveable member 210 translating and rotating over or under pivot point 214 to allow cutting element 212 to create a relatively large pocket P' through a small incision I'. Usually, the mechanism (not shown) to translate or rotate the moveable member 210 over or under pivot point 214 will be mounted on translatable or otherwise positionable table to allow axial movement of the moveable member 210 relative to the cornea (not shown).

Figure 21:
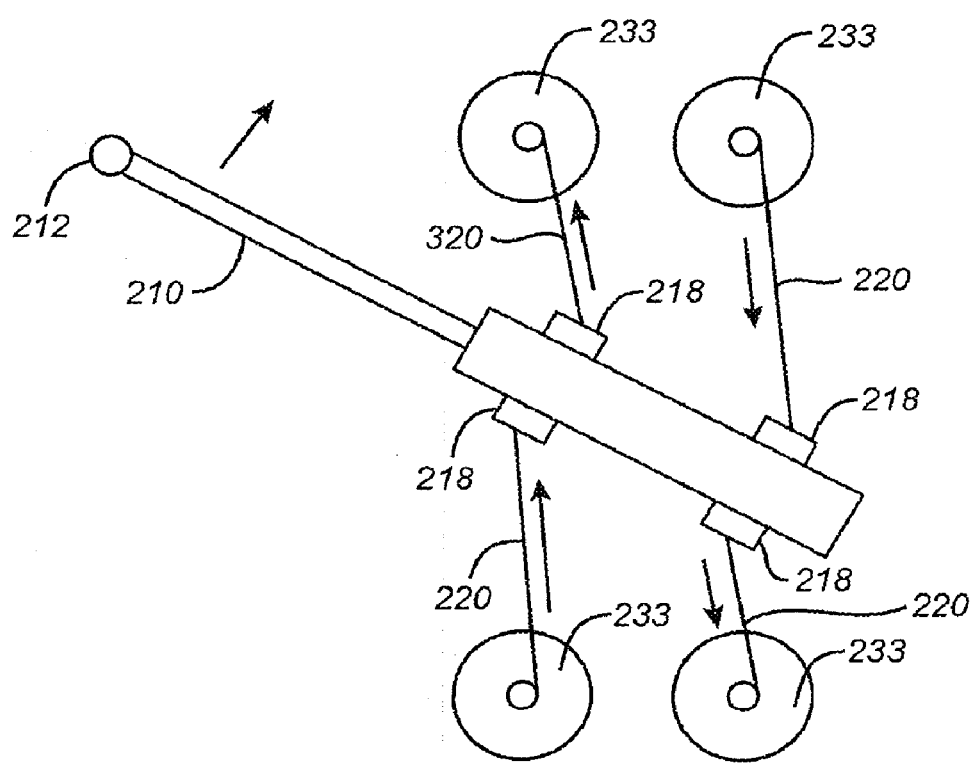
FIG. 21 illustrates a pivotless driver for manipulating a moveable member and cutting blade in accordance with the principles of the present invention.

An example of a cutting mechanism that does not contain a pivot element is shown in FIG. 21. Moveable member 210 is shown having two cutting guide restraints on each side, e.g., protrusions 218. Wires 220 are attached to protrusions 218 and programmable motors 233 that can either wind the wires to a shorter length or unwind the wires to a longer length. The programmable motors are controlled by cutting guide software. The winding and unwinding of the wires 220 applies force to the moveable member in the directions of the arrows adjacent to the wires and move the moveable member in an angular or translational way to create a cut by cutting element 212. In this embodiment, force is applied via wires, but any form of mechanical, pneumatic, electrical, or magnetic force could be used to create the same effect.

Figure 23A:
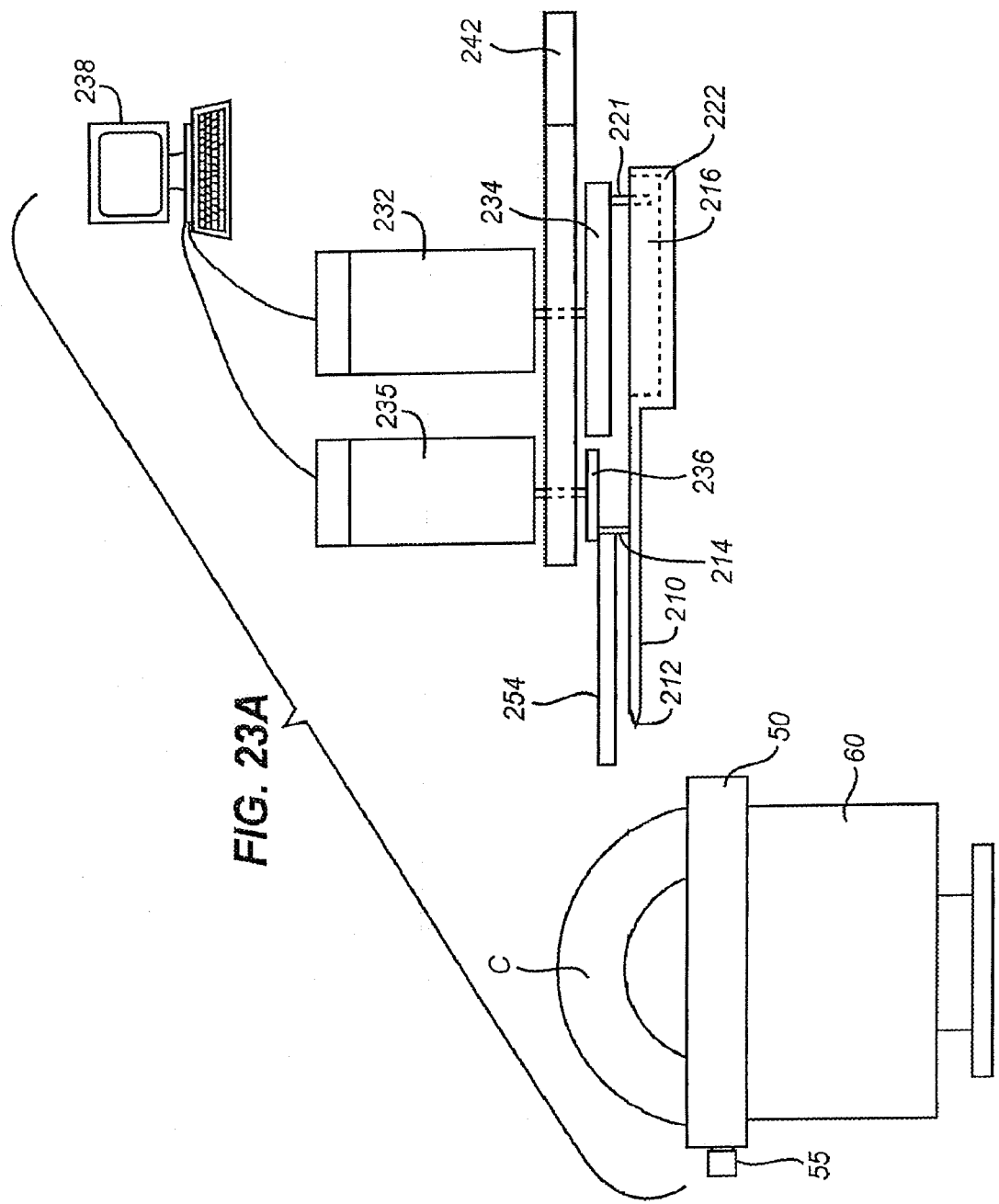
FIGS. 23A and 23B illustrate a system constructed in accordance with the principles of the present invention having an applanator slightly larger than the cutting element.
Figure 23B:
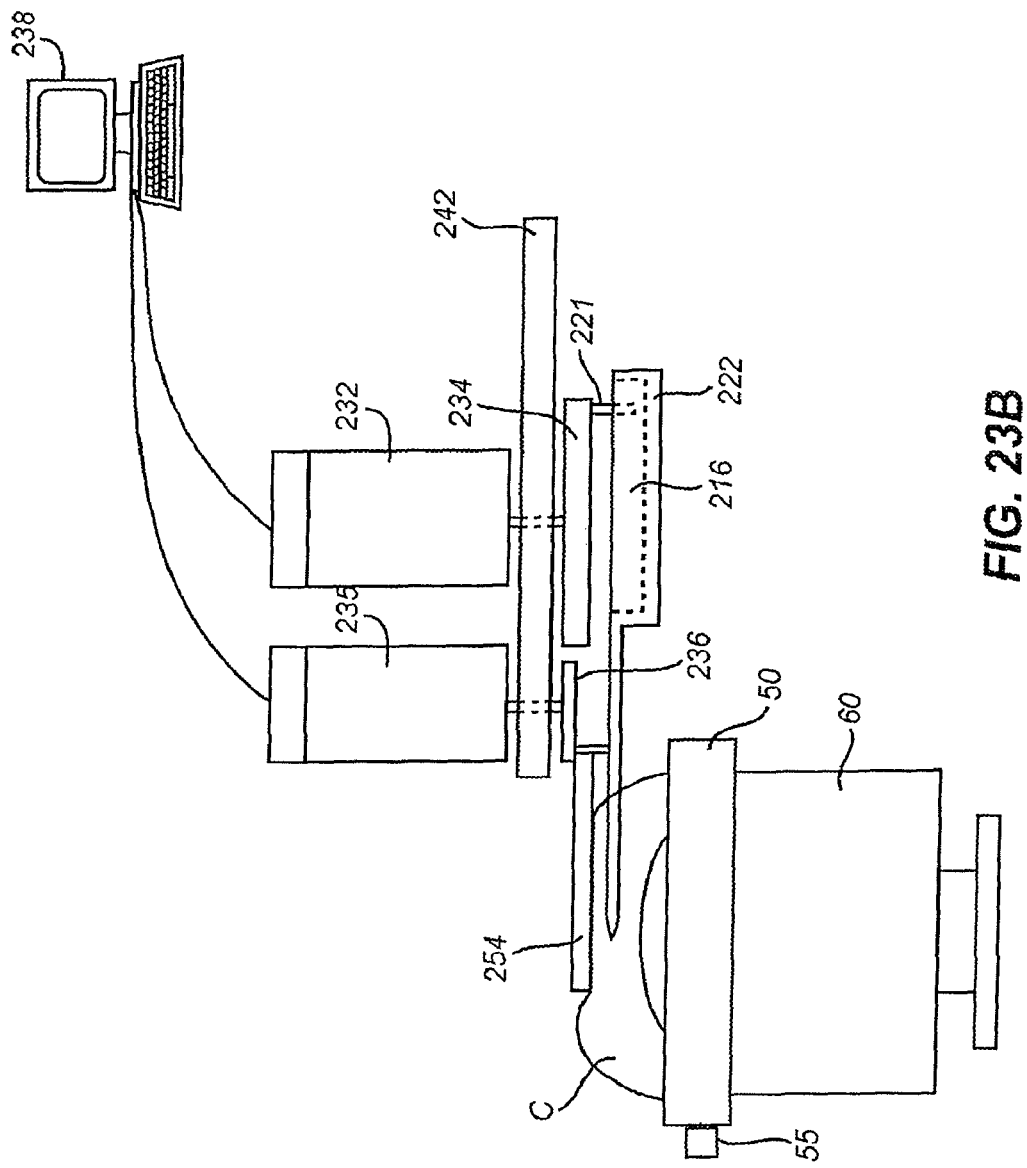

FIGS. 23A and 23B show an alternate embodiment of the present invention in which an applanator 254 is only slightly larger than the cutting element 212 and moveable member 210. In FIGS. 23C-23F Applanator 254 is shown in solid lines overlying the cornea C. Blade 212 and moveable member 210 are shown in dashed lines moving within pocket P. Applantor 254 moves concurrently with moveable member 210 and blade 212 to flatten cornea C in advance of blade 212 and moveable member 210.

FIGS. 23A and 23B also show an optional anterior chamber maintainer 60 that may be used as an attachment to the present embodiment. Details of the anterior chamber maintainer 60 were previously shown in FIGS. 7A and 8B. Anterior chamber maintainer 60 is specifically used when cutting tissue in a donor cornea. The donor corneal tissue is usually provided to the surgeon in the form of an excised cornea with a small rim of surrounding scleral tissue. As stated above, the present invention is designed to cut the cornea of a living complete eyeball. However, in order to harvest a donor cornea, it is also necessary to have an apparatus that will also enable the invention to cut a donated cornea that has been excised from the donor eyeball. The use of anterior chamber maintainers with prior art pocket forming devices has not been described. However, anterior chamber maintainers of the present invention may be adapted for use with other pocket forming devices such as such as those described by Peyman in U.S. Pat. Application 20010004702 and Feingold in U.S. Pat. No. 6,599,305 to allow harvesting of donor corneal tissue. The anterior chamber maintainer may be used for harvesting a donor cornea for any pocket forming device that requires stabilization of the donor cornea during the pocket forming process The sizes, distances, positions, and angles of the components of the present embodiments are merely representative of the types of mechanical devices and software which can be created. It is to be expected that other sizes, distances, positions, and angles of components can be used, all of which are in keeping within the scope of the present invention.

Although, the described embodiments of the invention describe primarily non-manual methods of translating and rotating the cutting element, it is to be understood that manual translation and rotation of the cutting element is also within the scope of the invention.

Figure 24A:
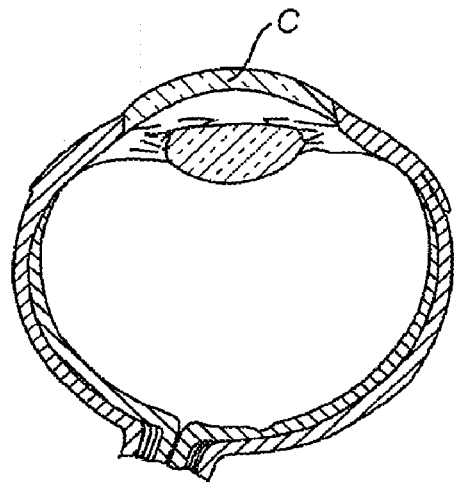
FIGS. 24A-24C illustrate methods in accordance with the principles of the present invention.
Figure 24B:
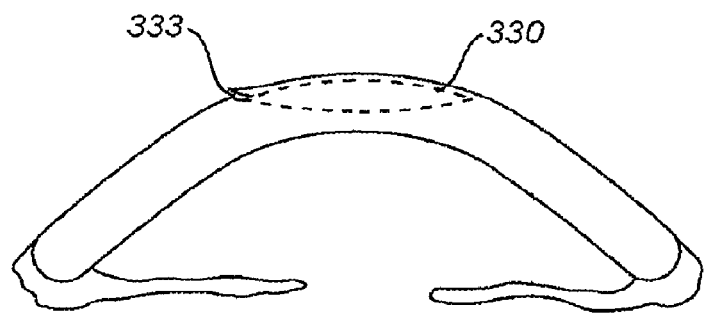
Figure 24C:
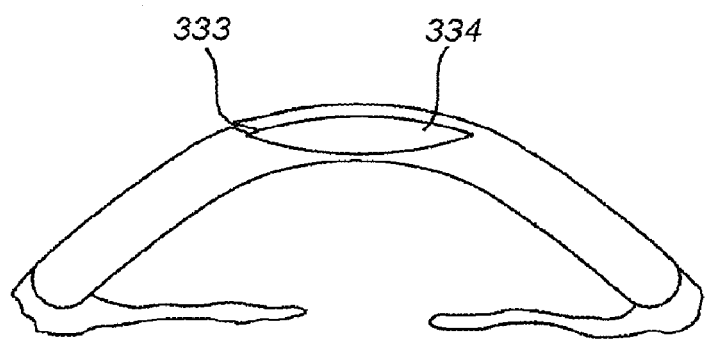

The present invention provides a method for creating a corneal pocket that may have a small external incision and a relatively large pocket. The corneal pocket created by the present invention may be advantageously used to retain an intracorneal lens that is reversibly deformable in shape. Once the lens is within the pocket, the small external opening prevents inadvertent dislocation or extrusion. FIG. 24 A shows a cross-section of a human eyeball which shows the relative location of cornea C. FIG. 24B shows a cross-sectional view of the cornea with a pocket 330 shown in broken lines and a small external opening 333. FIG. 37C shows a cross-sectional view of the cornea with a lens implant 334 within the pocket. The reversibly deformable lens may be folded or squeezed to allow entry through opening 333. The deformable lens may also be composed of a thermally reactive polymer that allows the implant to be in a shape that easily fits through opening 333 at room temperature (e.g. a rod) and then allows the implant to change into a final well fitting shape (e.g. a disk) when it is exposed to body temperature (not shown). Once the deformable lens is implanted into pocket 330, small external opening 333 may spontaneously self seal. Alternatively small external opening 333 can be closed with sutures or tissue adhesives.

Figure 22A:
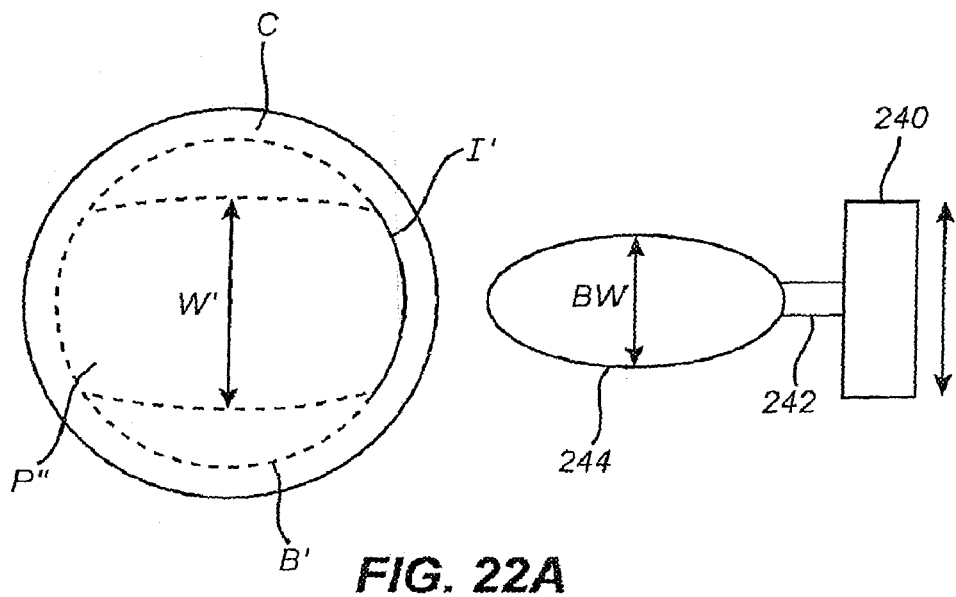
FIGS. 22A-22D illustrate a prior art cutting system which lacks the advantages of the present invention.
Figure 22B:
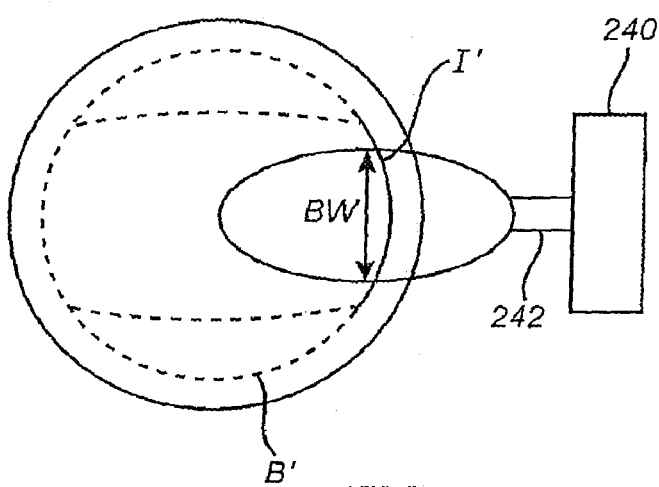

Comparison between the pocket size achievable with the present invention and that achievable with a prior art device is shown in FIGS. 22A-22B. A prior art corneal cutting device by Feingold is shown in FIG. 22A. In this apparatus, the blade assembly 240 oscillates the blade 244 laterally via blade assembly stem 242 while extending forward into the cornea to form the pocket P''', and the amplitude of the lateral oscillation increases as the blade goes beyond an entry incision I' into the cornea C. The inner dotted lines indicate the boundary of pocket P'''. The outer dotted lines B' indicate the boundary of a pocket created by the present invention. As shown in FIG. 22B, the smallest theoretical possible size of the entry incision would be the maximal width BW of the cutting blade 244. This type of entry incision would be created in the case that the blade 244 does not oscillate laterally during the entry cut. In this FIG. 22B the width BW of the blade is the same size as incision I'.

Figure 22C:
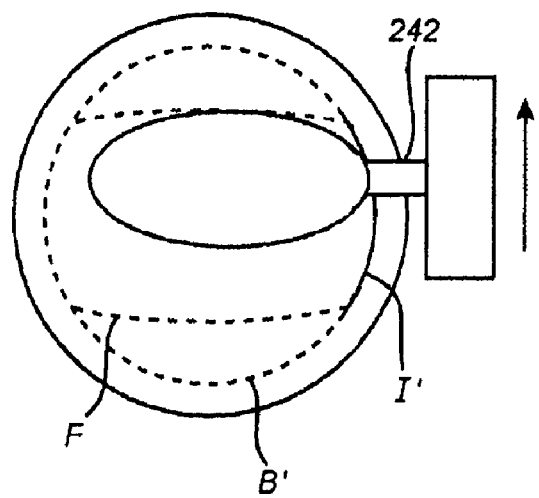

Once the blade is inside of the cornea as shown in FIG. 22C, the limit of lateral travel of the blade is governed by the width of the entry incision I' and the width of the blade assembly stem 242 that moves the blade. The stem of the blade assembly may not move more lateral than the lateral limit of the entry incision I'. When the blade moves to the right, the width of the pocket is extended to the right one half of the maximal width of the blade BW minus one half the width of the blade assembly stem 242.

Figure 22D:
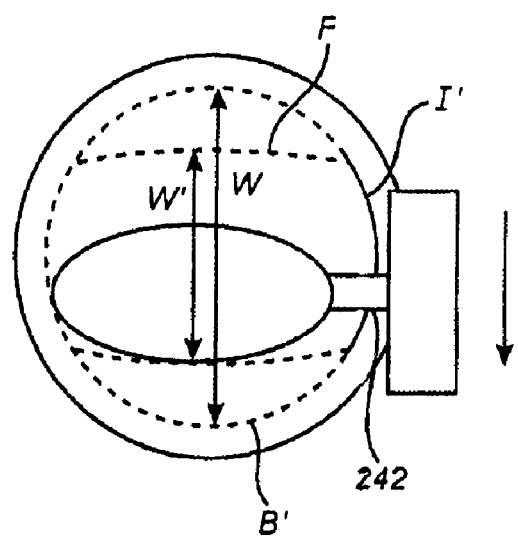

When the blade moves to the left as shown in FIG. 22D, the width of the pocket is extended to the left one half of the maximal width of the blade BW minus one half the width of the blade assembly stem 242. Therefore, the maximal width of the pocket W' is twice the maximal width of the blade minus the width of the blade assembly stem. The inner set of dotted lines F is the boundary of the pocket that can be created with Feingold's device. In the case that the width of the stem of the blade assembly approaches zero (not shown), the maximum width of the pocket is simply twice the blade width. Therefore, if the minimum width of the entry incision is the width of the blade and the maximum width of the pocket can only be twice the width of the blade, the ratio of the maximum pocket width to the entry incision width will always be less than the number two. From a practical standpoint, the ratio of the maximum pocket width to the entry incision will be significantly less than two because the blade assembly will usually need to oscillate to create the entry incision and the stem of the blade assembly cannot be zero. In this scaled drawing the maximal width of pocket P" is equal to 7 mm, the width of the incision I' is equal to 4 mm and the blade width BW is also equal to 4 mm. The ratio of the maximum pocket width W' to the incision width I' in this case is 1.75. The boundary B' is the boundary of a pocket using the present invention. Note that boundary B' is larger than boundary F for the same size incision I. The width of W in this scaled drawing is 10 mm and the incision width I' is 4 mm. Please also note that the ratio of the width of the pocket for the present invention W to the width of I' is 2.5, which is greater than the number two.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A system for cutting the cornea of an eye, said system comprising:
   a frame defining an X axis and a Y axis, which frame can be immobilized outside of the cornea;
   a moveable member having a cutting element at a distal end thereof; said moveable member being mounted on a pivot which is movably mounted relative to the frame; and
   a first programmable driver comprising a wheel-coupled to the pivot, said driver adapted to rotate the wheel to move the pivot over a path;
   a second programmable driver comprising a gear which is coupled to rotate the movable member over the pivot so that driving the wheel and gear advance the cutting element into an uncut cornea through a small initial incision in the cornea and cut a circular boundary of a pocket inside the cornea without enlarging the small initial incision.

2. A system as in claim 1, wherein the frame comprises a suction ring.

3. A system as in claim 1, wherein the system further comprises a corneal applanator.

4. A system as in claim 1, wherein the moveable member is linear.

5. A system as in claim 1, wherein the cutting element is deformable.

6. A system as in claim 1, wherein the wheel carries the pivot over a circular path.

7. A system as in claim 6, wherein the wheel is rotatably mounted within the gear.

8. A system as in claim 7, wherein the movable member is coupled to the gear by a protrusion on the gear which translates in a slot in the movable member.

9. A system as in claim 1, wherein the wheel engages a platform which carries the pivot over a lateral path.

* * * * *